(12) United States Patent
Bloch et al.

(10) Patent No.: US 11,639,345 B2
(45) Date of Patent: May 2, 2023

(54) METHIONINE METABOLIC PATHWAY INHIBITORS

(71) Applicant: MIGAL—GALILEE RESEARCH INSTITUTE LTD., Kiryat Shmona (IL)

(72) Inventors: Itai Bloch, Ramot Naftali (IL); Elad Cohen, Kiryat Shmona (IL); Rachel Amir, Kibbutz Dan (IL); Maayan Gal, Giva'at Ada (IL)

(73) Assignee: MIGAL—GALILEE RESEARCH INSTITUTE LTD., Kiryat Shmona (IL)

(*) Notice: Subject to any disclaimer, the term of this patent is extended or adjusted under 35 U.S.C. 154(b) by 202 days.

(21) Appl. No.: 16/918,687

(22) Filed: Jul. 1, 2020

(65) Prior Publication Data
US 2020/0331872 A1 Oct. 22, 2020

Related U.S. Application Data

(63) Continuation-in-part of application No. PCT/IL2019/050070, filed on Jan. 17, 2019.
(Continued)

(51) Int. Cl.
*C07D 403/06* (2006.01)
*A01N 43/58* (2006.01)
(Continued)

(52) U.S. Cl.
CPC .......... *C07D 403/06* (2013.01); *A01N 43/56* (2013.01); *A01N 43/58* (2013.01); *A01N 43/647* (2013.01);
(Continued)

(58) Field of Classification Search
None
See application file for complete search history.

(56) References Cited

U.S. PATENT DOCUMENTS

| 5,714,497 A | 2/1998 | Christophe et al. |
| 6,313,120 B1 | 11/2001 | Ferrari et al. |

(Continued)

FOREIGN PATENT DOCUMENTS

| CN | 107625766 B | 8/2012 |
| EP | 0468231 A2 | 7/1991 |

(Continued)

OTHER PUBLICATIONS

Sharp et al; "Evaluation of functional group as acetyl-lysine mimetics for BET bromodomaininhibition" MedchemComm 5 pp. 1834-1842. (2014).

(Continued)

*Primary Examiner* — Bethany P Barham
*Assistant Examiner* — Barbara S Frazier
(74) *Attorney, Agent, or Firm* — The Roy Gross Law Firm, LLC; Roy Gross

(57) ABSTRACT

The present invention provides novel inhibitors of cystathionin gamma synthase (CGS), their use as selective and non-selective herbicides, agricultural and non-agricultural herbicides, herbicides in integrated pest management, herbicides for gardening, clearing waste ground, clearing industrial or constructions sites, clearing railways and railway embankments, pesticide, fungicide, agricultural plant stimulant or antimicrobial agent. Also provided is a method for the control of undesired vegetation or clearing areas from the undesired vegetation comprising applying to the locus of said undesired vegetation, to the undesired plants or to a habitat thereof, a herbicidally effective amount of the compound of the present invention.

7 Claims, 26 Drawing Sheets
(8 of 26 Drawing Sheet(s) Filed in Color)

Related U.S. Application Data

(60) Provisional application No. 62/618,159, filed on Jan. 17, 2018.

(51) Int. Cl.

| | | |
|---|---|---|
| *A01N 43/707* | (2006.01) | |
| *A01N 43/713* | (2006.01) | |
| *A01N 43/80* | (2006.01) | |
| *A01N 43/82* | (2006.01) | |
| *A01N 43/86* | (2006.01) | |
| *A01N 43/90* | (2006.01) | |
| *C07D 231/56* | (2006.01) | |
| *C07D 233/70* | (2006.01) | |
| *C07D 237/14* | (2006.01) | |
| *C07D 239/36* | (2006.01) | |
| *C07D 249/06* | (2006.01) | |
| *C07D 249/18* | (2006.01) | |
| *C07D 257/04* | (2006.01) | |
| *C07D 271/06* | (2006.01) | |
| *C07D 277/42* | (2006.01) | |
| *C07D 401/06* | (2006.01) | |
| *C07D 401/12* | (2006.01) | |
| *C07D 403/12* | (2006.01) | |
| *C07D 405/12* | (2006.01) | |
| *C07D 413/04* | (2006.01) | |
| *C07D 413/06* | (2006.01) | |
| *C07D 413/14* | (2006.01) | |
| *C07D 417/10* | (2006.01) | |
| *C07D 471/04* | (2006.01) | |
| *A01N 43/56* | (2006.01) | |
| *A01N 43/647* | (2006.01) | |
| *A01N 43/54* | (2006.01) | |

(52) U.S. Cl.
CPC ......... *A01N 43/707* (2013.01); *A01N 43/713* (2013.01); *A01N 43/80* (2013.01); *A01N 43/82* (2013.01); *A01N 43/86* (2013.01); *A01N 43/90* (2013.01); *C07D 231/56* (2013.01); *C07D 233/70* (2013.01); *C07D 237/14* (2013.01); *C07D 239/36* (2013.01); *C07D 249/06* (2013.01); *C07D 249/18* (2013.01); *C07D 257/04* (2013.01); *C07D 271/06* (2013.01); *C07D 277/42* (2013.01); *C07D 401/06* (2013.01); *C07D 401/12* (2013.01); *C07D 403/12* (2013.01); *C07D 405/12* (2013.01); *C07D 413/04* (2013.01); *C07D 413/06* (2013.01); *C07D 413/14* (2013.01); *C07D 417/10* (2013.01); *C07D 471/04* (2013.01); *A01N 43/54* (2013.01)

(56) References Cited

U.S. PATENT DOCUMENTS

| | | | | |
|---|---|---|---|---|
| 2005/0245399 | A1* | 11/2005 | Shimoharada | A01N 47/22 548/366.1 |
| 2007/0105899 | A1 | 5/2007 | Suzuki et al. | |

FOREIGN PATENT DOCUMENTS

| | | |
|---|---|---|
| EP | 0614911 A1 | 2/1994 |
| JP | H05331164 A | 12/1993 |
| WO | 199532188 A1 | 11/1995 |
| WO | 2003057225 A2 | 7/2003 |
| WO | 2008014266 A2 | 1/2008 |
| WO | 2009058730 A1 | 5/2009 |
| WO | 2009086303 A2 | 7/2009 |
| WO | 2013096820 A1 | 6/2013 |
| WO | 2015042685 A1 | 4/2015 |

OTHER PUBLICATIONS

Keaney et al;"2-Alkyloxazoles as potent and selective PI4KIII[beta] inhibitors demonstrating inhibition of HCV replica" Bioorganic & Medicinal Chemistry Letters, v01. 24, No. 16, 12 (2014).

Yang et al; "Pd(II)-Catalyzed meta-C—H Olefination, Arylation, and Acetoxylation of Indolines Using a U-Shaped Template" Journal of the American Chemical Society 136, 30, 1pp. 0807-10813. (2014).

Matter et al; "QSAR-by-NMR: Quantitative Insights Into Structural Determinants for Binding Affinity by Analysis of 1H/15N Chemical Shift Differences in MMP-3 Ligands" Bioorganic & Medicinal Chemistry Letter 15(7):pp. 1779-1783. (2005).

Shingare et al; "Synthesis of Sulphonamodes Derived from 2-Methyl-4-(3-chlorosuiphonyl 4-substituted aryl) thiazoles" Indian Journal of Chemistry vol. 15 pp. 1063-1065. (1977).

Chemical Abstracts Service, Columbus, Ohio, US; Hashimoto, Koji et al: "Keratinocyte growth inhibitors and hydroxamic acid derivatives" (2001).

Chemical Abstracts Service, Columbus, Ohio, US; Goldfarb, David Scott: "Method using lifespan-aitering compounds for altering the lifespan of eukaryotic organisms, and screening for such compounds" (2009).

Datko et al. ; "Homocysteine biosynthesis in green plants", Journal of Biological Chemistry 249A, pp. 1139-1155 (1974).

M. R. Webb,"A continuous spectrophotometric assay for inorganic phosphate and for measuring phosphate release kinetics in biological systems" PNAS 89, pp. 4884-4887.(1992).

Hacham et al; "The N-Terminal Region of *Arabidopsis* Cystathionine Synthase Plays an Important Regulatory Role in Methionine Metabolism" Plant Physiol., 128(2): 454-462. (2002).

Steegborn et al. "The Crystal Structure of Cystathionine Gamma-Synthase from Nicotiana tabacum Reveals its Substrate and Reaction Specificity." J. Mol. Biol. 290, 983-996 (1999).

Steegborn et al. "Crystal Structures of Cystathionine Gamma-Synthase Inhibitor Complexes Rationalize the Increased Affinity of a Novel Inhibitor." J. Mol. Biol. 311, 789-801 (2001).

International Search Report of PCT/IL2019/050069 Completed Mar. 29, 2019; dated Apr. 12, 2019 7 pages.

Written Opinion of PCT/IL2019/050069 Completed Mar. 29, 2019; dated Apr. 12, 2019 8 pages.

Ganguly et al.; "Synthesis of heterocyclic compounds using radical reactions and evidence for the formation of spiro radical intermediates" Tetrahedron Letters 45 pp. 883-886. (2004). doi:10.1016/j.tetlet.2003.10.204.

Korbonits et al.; "Formation of 3-(2-Aminoaryl)-l,2,4-oxadiazoles into 3-Acyl-aminoindazoles ; Extension of the Boulton-Katritzky Scheme" Journal of the Chemical Society, Perkin Transactions 1 pp. 759-766. (1982). http://pubs.rsc.org | doi:10.1039/P19820000759.

Ye et al.; "1,2,3-Triazoles as versatile directing group for selective sp2 and sp3 C—H activation: cyclization vs substitution" Chemical Science vol. 4.No. 9 pp. 3712-3716. (2013). DOI: 10.1039/c3sc51211h.

\* cited by examiner

|   | CGS | Cysteine | Phospho-serine ester | External phosphate |
|---|---|---|---|---|
| 1 | + | + | + | - |
| 2 | + | - | + | - |
| 3 | + | + | - | - |
| 4 | - | + | + | - |
| 5 | - | + | + | + |

DMSO     IML-24

DMSO     IML-11

DMSO                IML-162

DMSO                IML-186

METHIONINE METABOLIC PATHWAY INHIBITORS

CROSS REFERENCE TO RELATED APPLICATIONS

This application is a Continuation-in-Part of PCT Patent Application No. PCT/IL2019/050070 having International filing date of Jan. 17, 2019, which claims the benefit of priority of U.S. Provisional Application No. 62/618,159 filed on Jan. 17, 2018 entitled NEW METHIONINE METABOLIC PATHWAY INHIBITORS. The contents of the above applications are all incorporated by reference as if fully set forth herein in their entirety.

TECHNICAL FIELD

The present application relates to the field of methionine metabolic pathway inhibition. In particular, the present application relates to novel inhibitors of cystathionin gamma synthase (CGS), the method for their molecular design and identification based on structural information obtained, and use thereof in various agricultural and non-agricultural applications.

BACKGROUND

Cystathionine γ-synthase (CGS) is the first enzyme of the trans-sulphuration pathway in bacteria and plants. In bacteria, sulphide is derived from the reduction of sulphate and is incorporated into L-cysteine (L-Cys), which is subsequently converted to L-homocysteine (L-Hcys), the immediate precursor of L-methionine (L-Met). This is in contrast with the mammalian reverse trans-sulphuration pathway in which L-Hcys is converted to L-Cys.

The CGS catalyses the committed step of methionine biosynthesis. Encoded by the metB gene in *Escherichia coli* (*E. coli*), the CGS catalyses a pyridoxal phosphate-dependent, α,γ-replacement reaction in which L-Cys and O-succinyl-L-homoserine are condensed to produce L-cystathionine (L-Cth) and succinate. A survey of the CGS activity in eleven species of higher plants including two gymnosperms and nine angiosperms was published by Datko et al. (1974) in "*Homocysteine biosynthesis in green plants*", Journal of Biological Chemistry 249A, pp. 1139-1155. That survey demonstrated that the trans-sulphuration pathway of plants is similar to that of bacteria, with the exception that substrates for the plant and bacterial CGS are different: O-phospho-L-homoserine vs O-succinyl-L-homoserine, respectively.

Recent studies have demonstrated that there is a large number of important applications for research on the CGS and the related enzymes of the trans-sulphuration pathway. This pathway is unique to microorganisms and plants, rendering the enzyme an attractive target for the development of antimicrobials and herbicides. Considering the imperative role the CGS plays in the production of L-Met in plants, it is believed that a small molecule inhibitor that would selectively bind the CGS could potentially be developed into a herbicide. Furthermore, owing to its absence in mammalians, any discovered CGS-based herbicide is assumed to be non-toxic for humans.

The structure of CGS from *Nicotiana tabacum* was solved to a satisfactory resolution of 2.9 Å by Steegborn et al. (1999), "*The crystal structure of cystathionine γ-synthase from Nicotiana tabacum reveals its substrate and reaction specificity*", Journal of Molecular Biology, 290(5), pp. 983-996. The CGS active site of *Nicotiana tabacum* was found to be more confined than the active cite of *E. Coli* solved by the same group one year earlier. It corresponds to the smaller O-phospho-L-homoserine substrate, than that of the O-succinyl-L-homoserine specific to *E. Coli*, and its active site has less extended loop structure adopted by residues 36* to 45* (where the asterisk indicates a residue from the second subunit).

Steegborn et al. (2001) in "*Crystal structures of cystathionine gamma-synthase inhibitor complexes rationalize the increased affinity of a novel inhibitor*", Journal of Molecular Biology, 311, pp. 789-801, solved the crystal structures of several complexes of the CGS from *Nicotiana tabacum* with inhibitors of different compound classes. The complex with the specific substrate analogue dl-E-2-amino-5-phosphono-3-pentenoic acid verified the role of the carboxylate-binding Arg423 residue and identified the phosphate-binding pocket of the active site. The resolved structure demonstrated the role of Lys165 in specificity determination and the role of the Tyr163 flexible side-chain in catalysis.

The CGS inhibitor 5-carboxymethylthio-3-(3'-chlorophenyl)-1,2,4-oxadiazol identified by Steegborn et al. (2001) shows the highest affinity to the CGS reported so far, due to binding to an additional active site pocket, which is not used by physiological substrates. It was speculated that the tightly bent conformation of this inhibitor allows it to simultaneously bind to both the carboxylate-recognition site and another binding pocket between Arg423 and Ser388.

The CGS inhibitor structure described by Steegborn et al. (2001) suggests improvements for known inhibitors and gives guidelines for the development of new lead compounds. Nevertheless, this structure still possesses a relatively low affinity due to the non-optimal arrangement of the functional groups interacting with the phosphate and carboxylate-recognition site. For development of new herbicides whose mechanism of action is the plant CGS inhibition, it is therefore necessary to find more effective and specific compounds acting as the CGS inhibitors. To make this possible in a rational way, there is a great need for further look into the plant CGS structure and into the precise manner of interactions of the potential inhibitors to the active cite of the enzyme.

SUMMARY

In one aspect, the present invention relates to methionine metabolic pathway inhibitors having the following Formula (I):

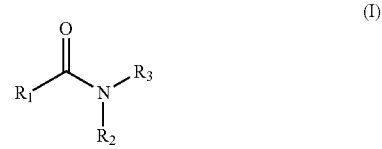

(I)

wherein $R_1$ is an aromatic or heteroaromatic radical of Formula (A), Formula (B), Formula (C), Formula (D), or Formula (E):

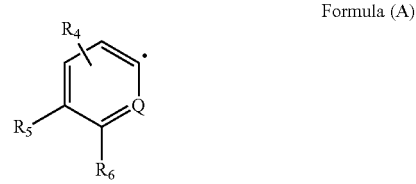

Formula (A)

-continued

Formula (B)

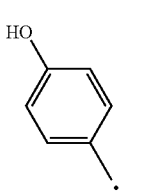

Formula (C)

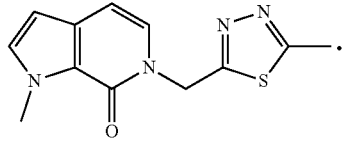

Formula (D)

Formula (E)

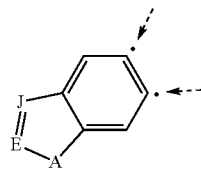

wherein Q in Formula (A) is C—$R_7$, C., or N;

$R_4$, $R_6$ and $R_7$ are independently selected from hydrogen, halogen, amino, cyano, nitro, ($C_1$-$C_3$)-alkyl, ($C_1$-$C_3$)-haloalkyl, hydroxy, ($C_1$-$C_3$)-alkoxy, ($C_1$-$C_3$)-haloalkoxy, mono-($C_1$-$C_3$)-alkylamino, di-($C_1$-$C_3$)-alkylamino, amino-($C_1$-$C_3$)-alkyl, mono-($C_1$-$C_3$)-alkylamino-($C_1$-$C_3$)-alkyl and di-($C_1$-$C_3$)-alkylamino-($C_1$-$C_3$)-alkyl group; and $R_5$ is hydrogen, halogen, cyano, ($C_1$-$C_3$)-alkyl, ($C_1$-$C_3$)-haloalkyl, ($C_1$-$C_3$)-alkoxy, hydroxy, ($C_1$-$C_3$)-haloalkoxy, amino, mono-($C_1$-$C_3$)-alkylamino, di-($C_1$-$C_3$)-alkylamino, amino-($C_1$-$C_3$)-alkyl, mono-($C_1$-$C_3$)-alkylamino-($C_1$-$C_3$)-alkyl, di-($C_1$-$C_3$)-alkylamino-($C_1$-$C_3$)-alkyl, nitro or 3,5-dimethyl-1H-pyrazol-1-yl group; or $R_5$ and $R_6$ when taken together with two carbon atoms to which they are attached form a five-membered heterocyclic radical 2,5-dihydrofuranyl of the following formula:

2,5-Dihydrofuranyl

X and Y in Formula (D) are independently CH or N;
Z is C—$R_8$ or N;
$R_8$ is hydrogen, halogen, nitro, ($C_1$-$C_3$)-alkyl, ($C_1$-$C_3$)-haloalkyl, ($C_1$-$C_3$)-alkoxy, hydroxy, carboxylate, ($C_1$-$C_3$)-alkylcarboxylate, carboxylic acid, ($C_1$-$C_3$)-alkylcarboxylic acid, carboxamide, ($C_1$-$C_3$)-alkylcarboxamide, cyano, pyridinyl, phenyl, benzyl or phenylamino, wherein said pyridinyl, phenyl, benzyl or phenylamino are optionally substituted with one to three same or different substituents at any available heteroaromatic or aromatic ring carbon atom, said substituents are selected from halogen, ($C_1$-$C_3$)-alkyl, ($C_3$-$C_6$)-cycloalkyl, ($C_1$-$C_3$)-haloalkyl, hydroxy, ($C_1$-$C_3$)-alkoxy, cyano, amino, carboxylic acid, or nitro group;
L is N—$R_9$, O or S; and
$R_9$ is hydrogen, ($C_1$-$C_3$)-alkyl, ($C_1$-$C_3$)-haloalkyl, carboxymethyl, benzyl or phenyl, wherein said benzyl or phenyl are optionally substituted with one to three same or different substituents at any available aromatic ring carbon atom, said substituents are selected from halogen, cyano, ($C_1$-$C_3$)-alkyl, ($C_1$-$C_3$)-haloalkyl, hydroxy, ($C_1$-$C_3$)-alkoxy, amino, or nitro group;

two dashed arrows in Formula (E) point to two carbon atoms of the phenyl ring, to which the carbonyl can be attached;
A is CH—$R_{10}$ or N—$R_{11}$;
E is C—$R_{12}$ or N;
J is C—$R_{13}$ or N; and
$R_{10}$, $R_{11}$, $R_{12}$ and $R_{13}$, are independently selected from hydrogen, ($C_1$-$C_3$)-alkyl and ($C_1$-$C_3$)-haloalkyl;
(i) provided that when $R_1$ is the radical of the Formula (A), then:
$R_3$ is pyridinyl or phenyl substituted at any available aromatic ring carbon atom with one or two groups, wherein the first group is optional and selected from carboxylmethyl and carboxyl group, and the second group is selected from the following radicals:

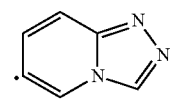

wherein X and Y are independently CH or N;
Z is C—$R_8$ or N;
$R_8$ is hydrogen, halogen, nitro, ($C_1$-$C_3$)-alkyl, ($C_1$-$C_3$)-haloalkyl, ($C_1$-$C_3$)-alkoxy, hydroxy, carboxylate, ($C_1$-$C_3$)-alkylcarboxylate, carboxylic acid, ($C_1$-$C_3$)-alkylcarboxylic acid, carboxamide, ($C_1$-$C_3$)-alkylcarboxamide, cyano, pyridinyl, phenyl, benzyl or phenylamino, wherein said pyridinyl, phenyl, benzyl or phenylamino are optionally substituted with one to three same or different substituents at any available heteroaromatic or aromatic ring carbon atom, said substituents are selected from halogen, ($C_1$-$C_3$)-alkyl, ($C_3$-$C_6$)-cycloalkyl, ($C_1$-$C_3$)-haloalkyl, hydroxy, ($C_1$-$C_3$)-alkoxy, cyano, amino, carboxylic acid, or nitro group;
L is N—$R_9$, O or S; and
$R_9$ is hydrogen, ($C_1$-$C_3$)-alkyl, ($C_1$-$C_3$)-haloalkyl, carboxymethyl, benzyl or phenyl, wherein said benzyl or phenyl are optionally substituted with one to three same or different substituents at any available aromatic ring carbon atom, said substituents are selected from halogen, cyano, ($C_1$-$C_3$)-alkyl, ($C_1$-$C_3$)-haloalkyl, hydroxy, ($C_1$-$C_3$)-alkoxy, amino, or nitro group; and $R_2$ is either hydrogen or carbonyl (C=O), and
when $R_2$ is carbonyl, Q is C. and $R_2$ and Q form a bond.
(ii) provided that when $R_1$ is the radical of the Formula (B), then
$R_2$ is hydrogen, and
$R_3$ is [1,2,4]-triazolo[4,3-a]pyridinyl of the formula:

(iii) provided that when $R_1$ is the radical of the Formula (C), then
  $R_2$ is hydrogen, and
  $R_3$ is phenyl;
(iv) provided that when $R_1$ is the radical of the Formula (D), then
  $R_2$ and $R_3$ when taken together form around the nitrogen atom, to which they are attached, an indolyl radical of the formula:

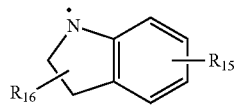

wherein $R_{15}$ and $R_{16}$ are independently selected from hydrogen, halogen, nitro, $(C_1\text{-}C_3)$-alkyl, $(C_1\text{-}C_3)$-haloalkyl, $(C_1\text{-}C_3)$-alkoxy, hydroxy, cyano, carboxylic acid, carboxylate, $(C_1\text{-}C_3)$-alkylcarboxylate, carboxamide, $(C_1\text{-}C_3)$-alkylcarboxylic acid, $(C_1\text{-}C_3)$-alkylcarboxamide, or amino group; and
(v) provided that when $R_1$ is the radical of the Formula (E), then
  $R_2$ is hydrogen or $(C_1\text{-}C_3)$-alkyl, and
  $R_3$ is a radical of the formula:

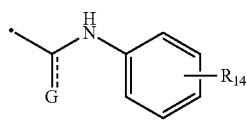

wherein $R_{14}$ is one to three same or different substituents attached to any available carbon atom of the phenyl ring and independently selected from hydrogen, amino, $(C_1\text{-}C_3)$-alkyl, $(C_1\text{-}C_3)$-haloalkyl, $(C_1\text{-}C_3)$-alkoxy, $(C_1\text{-}C_3)$-alkylcarboxylic acid, carboxylic acid, $(C_1\text{-}C_3)$-alkylcarboxylate, carboxylate, $(C_1\text{-}C_3)$-alkylcarboxamide, carboxamide, halogen, cyano, hydroxy, nitro and acetylamino group; and either:
  ═══ is a double bond, and G is O; or
  ─── is a single bond, and G taken together with the two adjacent carbon atoms and with the nitrogen atom to which the second carbon atom is attached forms a five- or six-membered heterocyclic ring.

In other embodiments, the compounds of formula (I), capable of inhibiting methionine metabolic pathway, can be used in inhibiting cystathionin γ-synthase (CGS) in general, and in plants, fungi and bacteria, in particular. These compounds can be used as herbicides, pesticides, fungicides, agricultural plant stimulants or antimicrobial agents. The compounds of the present invention can be used for seed treatment. In a particular embodiment, the compounds of the present invention are used as selective herbicides, non-selective herbicides, agricultural herbicides, non-agricultural herbicides or weed killers, herbicides in integrated pest management, herbicides in gardening, herbicides in clearing waste ground, herbicides in clearing industrial or constructions sites, or herbicides in clearing railways and railway embankments.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures.

FIG. 2b presents a table showing the corresponding initial components used in the reaction.

DETAILED DESCRIPTION

Figure 1:
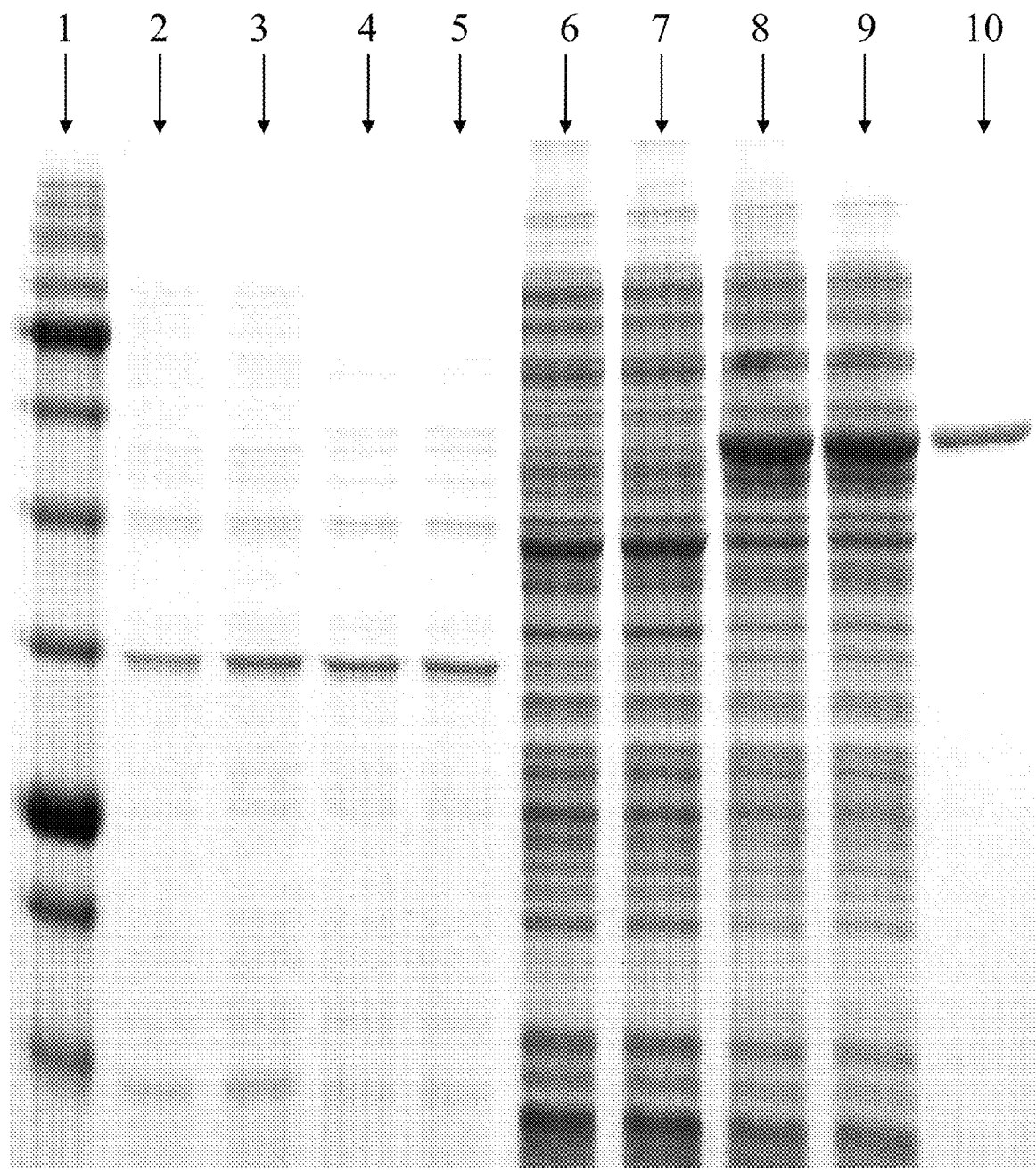
FIG. 1 shows the coomassie-stained 12% SDS gel electrophoresis of the proteins eluted from the nickel column:
Lane 1 is a marker band,
Lanes 2 and 3—non-soluble content of the first and second colony before the addition of IPTG,
Lanes 4 and 5—non-soluble content of the first and second colony 4 hours after the addition of 1 mM IPTG,
Lanes 6 and 7—soluble content of the first and second colony before the addition of IPTG,
Lanes 8 and 9—soluble content of the first and second colony 4 hours after the addition of 1 mM IPTG, and
Lane 10—the band showing the protein expressed from the first colony after it was eluted from the nickel column.

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, for example, the scope of the expression "a composition comprising x and z" should not be limited to compositions consisting only of ingredients x and z. Also, the scope of the expression "a method comprising the steps x and z" should not be limited to methods consisting only of these steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Considering the imperative role that cystathionin γ-synthase (CGS) plays in the production of methionine in plants, the present embodiments are related to small organic compounds capable of binding to and hence, selectively inhibiting the enzyme cystathionin γ-synthase (CGS). These organic compounds may potentially be developed into the CGS-based herbicides, which would be non-toxic to humans since CGS is absent in mammalians.

The present invention provides inhibitors of methionine metabolic pathway having the following Formula (I):

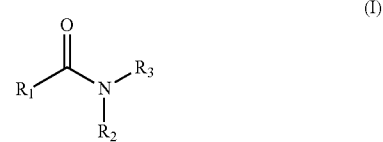
(I)

wherein $R_1$ is an aromatic or heteroaromatic radical of Formula (A), Formula (B), Formula (C), Formula (D), or Formula (E):

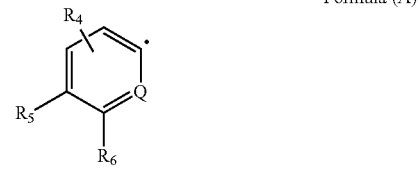
Formula (A)

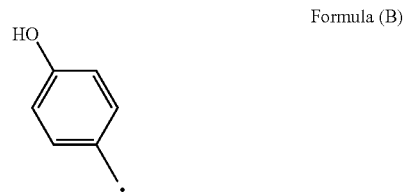
Formula (B)

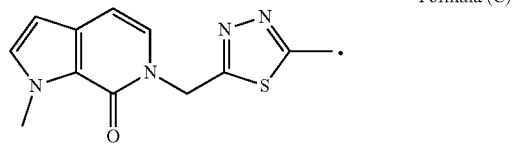
Formula (C)

Formula (D)

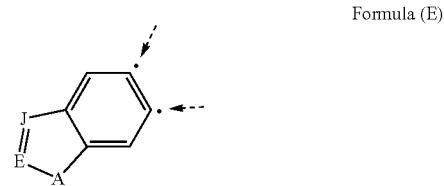
Formula (E)

wherein Q in Formula (A) is C—$R_7$, C., or N;

$R_4$, $R_6$ and $R_7$ are independently selected from hydrogen, halogen, amino, cyano, nitro, ($C_1$-$C_3$)-alkyl, ($C_1$-$C_3$)-haloalkyl, hydroxy, ($C_1$-$C_3$)-alkoxy, ($C_1$-$C_3$)-haloalkoxy, mono-($C_1$-$C_3$)-alkylamino, di-($C_1$-$C_3$)-alkylamino, amino-($C_1$-$C_3$)-alkyl, mono-($C_1$-$C_3$)-alkylamino-($C_1$-$C_3$)-alkyl and di-($C_1$-$C_3$)-alkylamino-($C_1$-$C_3$)-alkyl group; and $R_5$ is hydrogen, halogen, cyano, ($C_1$-$C_3$)-alkyl, ($C_1$-$C_3$)-haloalkyl, ($C_1$-$C_3$)-alkoxy, hydroxy, ($C_1$-$C_3$)-haloalkoxy, amino, mono-$(C_1-C_3)$-alkylamino, di-$(C_1-C_3)$-alkylamino, amino-$(C_1-C_3)$-alkyl, mono-$(C_1-C_3)$-alkylamino-$(C_1-C_3)$-alkyl, di-$(C_1-C_3)$-alkylamino-$(C_1-C_3)$-alkyl, nitro or 3,5-dimethyl-1H-pyrazol-1-yl group; or $R_5$ and $R_6$ when taken together with two carbon atoms to which they are attached form a five-membered heterocyclic radical 2,5-dihydrofuranyl of the following formula:

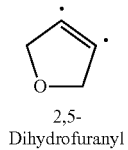

2,5-Dihydrofuranyl

X and Y in Formula (D) are independently CH or N;
Z is C—$R_8$ or N;
$R_8$ is hydrogen, halogen, nitro, $(C_1-C_3)$-alkyl, $(C_1-C_3)$-haloalkyl, $(C_1-C_3)$-alkoxy, hydroxy, carboxylate, $(C_1-C_3)$-alkylcarboxylate, carboxylic acid, $(C_1-C_3)$-alkylcarboxylic acid, carboxamide, $(C_1-C_3)$-alkylcarboxamide, cyano, pyridinyl, phenyl, benzyl or phenylamino, wherein said pyridinyl, phenyl, benzyl or phenylamino are optionally substituted with one to three same or different substituents at any available heteroaromatic or aromatic ring carbon atom, said substituents are selected from halogen, $(C_1-C_3)$-alkyl, $(C_3-C_6)$-cycloalkyl, $(C_1-C_3)$-haloalkyl, hydroxy, $(C_1-C_3)$-alkoxy, cyano, amino, carboxylic acid, or nitro group;

L is N—$R_9$, O or S; and $R_9$ is hydrogen, $(C_1-C_3)$-alkyl, $(C_1-C_3)$-haloalkyl, carboxymethyl, benzyl or phenyl, wherein said benzyl or phenyl are optionally substituted with one to three same or different substituents at any available aromatic ring carbon atom, said substituents are selected from halogen, cyano, $(C_1-C_3)$-alkyl, $(C_1-C_3)$-haloalkyl, hydroxy, $(C_1-C_3)$-alkoxy, amino, or nitro group;

two dashed arrows in Formula (E) point to two carbon atoms of the phenyl ring, to which the carbonyl can be attached;

A is CH—$R_{10}$ or N—$R_{11}$;
E is C—$R_{12}$ or N;
J is C—$R_{13}$ or N; and
$R_{10}$, $R_{11}$, $R_{12}$ and $R_{13}$, are independently selected from hydrogen, $(C_1-C_3)$-alkyl and $(C_1-C_3)$-haloalkyl;

(i) provided that when $R_1$ is the radical of the Formula (A), then:

$R_3$ is pyridinyl or phenyl substituted at any available aromatic ring carbon atom with one or two groups, wherein the first group is optional and selected from carboxylmethyl and carboxyl group, and the second group is selected from the following radicals:

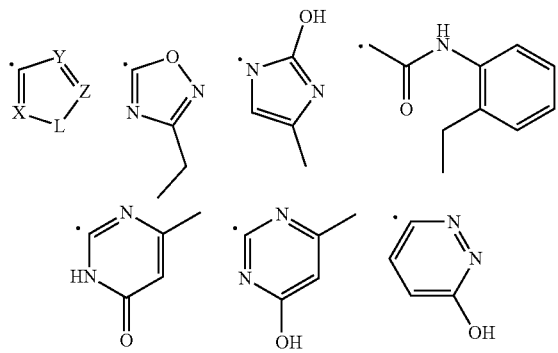

wherein X and Y are independently CH or N;
Z is C—$R_8$ or N;
$R_8$ is hydrogen, halogen, nitro, $(C_1-C_3)$-alkyl, $(C_1-C_3)$-haloalkyl, $(C_1-C_3)$-alkoxy, hydroxy, carboxylate, $(C_1-C_3)$-alkylcarboxylate, carboxylic acid, $(C_1-C_3)$-alkylcarboxylic acid, carboxamide, $(C_1-C_3)$-alkylcarboxamide, cyano, pyridinyl, phenyl, benzyl or phenylamino, wherein said pyridinyl, phenyl, benzyl or phenylamino are optionally substituted with one to three same or different substituents at any available heteroaromatic or aromatic ring carbon atom, said substituents are selected from halogen, $(C_1-C_3)$-alkyl, $(C_3-C_6)$-cycloalkyl, $(C_1-C_3)$-haloalkyl, hydroxy, $(C_1-C_3)$-alkoxy, cyano, amino, carboxylic acid, or nitro group;

L is N—$R_9$, O or S; and $R_9$ is hydrogen, $(C_1-C_3)$-alkyl, $(C_1-C_3)$-haloalkyl, carboxymethyl, benzyl or phenyl, wherein said benzyl or phenyl are optionally substituted with one to three same or different substituents at any available aromatic ring carbon atom, said substituents are selected from halogen, cyano, $(C_1-C_3)$-alkyl, $(C_1-C_3)$-haloalkyl, hydroxy, $(C_1-C_3)$-alkoxy, amino, or nitro group; and $R_2$ is either hydrogen or carbonyl (C=O), and
when $R_2$ is carbonyl, Q is C. and $R_2$ and Q form a bond.
(ii) provided that when $R_1$ is the radical of the Formula (B), then
$R_2$ is hydrogen, and
$R_3$ is [1,2,4]-triazolo[4,3-a]pyridinyl of the formula:

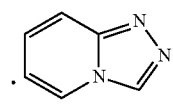

(iii) provided that when $R_1$ is the radical of the Formula (C), then
$R_2$ is hydrogen, and
$R_3$ is phenyl;
(iv) provided that when $R_1$ is the radical of the Formula (D), then
$R_2$ and $R_3$ when taken together form around the nitrogen atom, to which they are attached, an indolyl radical of the formula:

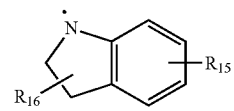

wherein $R_{15}$ and $R_{16}$ are independently selected from hydrogen, halogen, nitro, $(C_1-C_3)$-alkyl, $(C_1-C_3)$-haloalkyl, $(C_1-C_3)$-alkoxy, hydroxy, cyano, carboxylic acid, carboxylate, $(C_1-C_3)$-alkylcarboxylate, carboxamide, $(C_1-C_3)$-alkylcarboxylic acid, $(C_1-C_3)$-alkylcarboxamide, or amino group; and (v) provided that when $R_1$ is the radical of the Formula (E), then
$R_2$ is hydrogen or $(C_1-C_3)$-alkyl, and
$R_3$ is a radical of the formula:

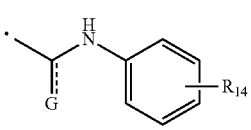

wherein $R_{14}$ is one to three same or different substituents attached to any available carbon atom of the phenyl ring and independently selected from hydrogen, amino, $(C_1-C_3)$-alkyl, $(C_1-C_3)$-haloalkyl, $(C_1-C_3)$-alkoxy, $(C_1-C_3)$-alkylcarboxylic acid, carboxylic acid, $(C_1-C_3)$-alkylcarboxylate, carboxylate, $(C_1-C_3)$-alkylcarboxamide, carboxamide, halogen, cyano, hydroxy, nitro and acetylamino group; and either:

═══ is a double bond, and G is O; or

═══ is a single bond, and G taken together with the two adjacent carbon atoms and with the nitrogen atom to which the second carbon atom is attached forms a five- or six-membered heterocyclic ring.

The term "alkyl" refers to a saturated monovalent hydrocarbon radical. Exemplary alkyl groups include methyl, ethyl and propyl. The term "$(C_1-C_3)$-alkyl" refers to an alkyl containing from one to three carbon atoms. When alkyl is used as a suffix following another named group, such as "haloalkyl", this is intended to refer to an alkyl having bonded thereto one, two or three of the other, specifically-named groups, such as halogen, at any point of attachment on either the straight or branched chain of the alkyl.

The term "aryl", refers to a monovalent unsaturated aromatic hydrocarbon radical of six to eighteen ring atoms having a single ring or multiple condensed rings. Exemplary aryl groups are phenyl, biphenyl, benzyl, naphthyl, anthryl, pyrenyl and the like. When the term "substituted" is used with such groups, as in "optionally substituted with one to three substituents independently selected from", it should be understood that the aryl moiety may be optionally substituted with the same or different groups independently selected from those recited above and hereinafter as appropriate.

The term "cycloalkyl" refers to a fully saturated and partially unsaturated cyclic monovalent hydrocarbon radical having three to six carbon atoms in a ring. Exemplary cycloalkyl groups are cyclopropyl, cyclobutyl, cyclopentyl and cyclohexanyl.

The terms "heterocyclic" and "heterocyclyl" refer to fully saturated or partially unsaturated non-aromatic cyclic radicals of three to eight ring atoms in each cycle (in each monocyclic group, six to twelve atoms in a bicyclic group, and ten to eighteen atoms in a tricyclic group), which have at least one heteroatom (nitrogen, oxygen or sulphur) and at least one carbon atom in a ring. Each ring of the heterocyclic group containing a heteroatom may have from one to three heteroatoms, where the nitrogen and/or sulphur heteroatoms may optionally be oxidised and the nitrogen heteroatoms may optionally be quaternised. A heterocyclyl group may have a carbon ring atom replaced with a carbonyl group. The heterocyclyl group may be attached to the remainder of the molecule at any nitrogen atom or carbon atom of the ring or ring system. Additionally, the heterocyclo group may have a second or third ring attached thereto in a spiro or fused fashion, provided the point of attachment is to the heterocyclyl group. An attached spiro ring may be a carbocyclic or heterocyclic ring and the second and/or third fused ring may be a cycloalkyl, aryl or heteroaryl ring. Exemplary monocyclic heterocyclic groups include azetidinyl, oxiranyl, pyrrolidinyl, pyrazolinyl, imidazolidinyl, dioxanyl, dioxolanyl, oxazolidinyl, piperidinyl, piperazinyl, morpholinyl, tetrahydrofuryl, tetrahydropyranyl, thiamorpholinyl, and the like. Exemplary bicyclic heterocyclic groups include indolinyl, isoindolinyl, quinuclidinyl, benzopyrrolidinyl, benzopyrazolinyl, benzoimidazolidinyl, benzopiperidinyl, tetrahydroisoquinolinyl, tetrahydroquinolinyl, dihydroisoindolyl and the like.

The term "heteroaryl" refers to aromatic monocyclic, bicyclic or tricyclic radicals of three to eight ring atoms in each cycle (for example, three to eight atoms in a monocyclic group, six to twelve atoms in a bicyclic group, and to to eighteen atoms in a tricyclic group), which have at least one heteroatom (nitrogen, oxygen or sulphur) and at least one carbon atom in a ring. Each ring of the heteroaryl group may have one to four heteroatoms, wherein nitrogen and/or sulphur may optionally be oxidised, and the nitrogen heteroatoms may optionally be quaternised. The heteroaryl group may be attached to the remainder of the molecule at any nitrogen atom or carbon atom of the ring or ring system. Additionally, the heteroaryl group may have a second or third carbocyclic (cycloalkyl or aryl) or heterocyclic ring fused thereto provided the point of attachment is to the heteroaryl group. Exemplary heteroaryl groups are pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl and so on. Exemplary bicyclic heteroaryl groups include benzothiazolyl, benzoxazolyl, quinolinyl, benzoxadiazolyl, benzothienyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), triazinylazepinyl, and the like.

The heterocyclyl ring may optionally be fused to a (one) aryl or heteroaryl ring as defined herein provided the aryl and heteroaryl rings are monocyclic. Additionally, one or two ring carbon atoms in the heterocyclyl ring can optionally be replaced with a carbonyl group. When the heterocyclyl ring is partially saturated it can contain one to three ring double bonds provided that the ring is not aromatic.

The terms "alkoxy" refers to the groups of the structure —OR and wherein the group R is independently selected from the alkyl or cycloalkyl groups defined and recited above and hereinafter as appropriate.

The terms "alkylamino" or "dialkylamino" refers to an amino group wherein one or both of the hydrogen atoms are replaced with a group selected from the alkyl or cycloalkyl groups defined and recited above and hereinafter as appropriate.

The terms "halo" and "halogen" refers to fluoro/fluorine, chloro/chlorine, bromo/bromine, or iod/iodine radicals/atoms, relatively. The term "haloalkyl" refers to alkyl and cycloalkyl radicals as defined above, substituted with one or more halogen atoms, including those substituted with different halogens. Exemplary groups are chloromethyl, trifluoromethyl, perfluoropropyl, trichloroethylenyl, chloroacetylenyl, and the like.

The present invention further provides inhibitors of methionine metabolic pathway having Formula (IA1):

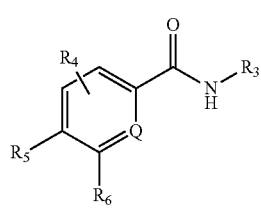

(IA1)

wherein Q is C—$R_7$ or N;

$R_3$ is pyridinyl or phenyl substituted at any available aromatic ring carbon atom with one or two groups, wherein the first group is optional and selected from carboxymethyl and carboxyl group, and the second group is selected from the following radicals:

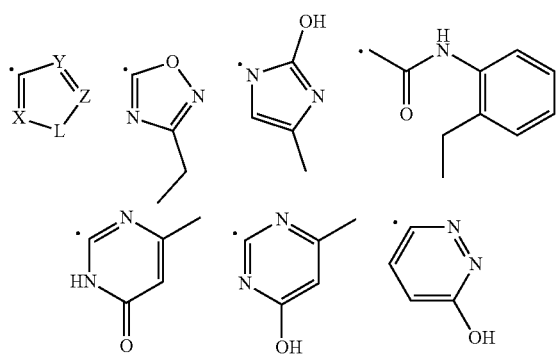

and $R_5$ is hydrogen, halogen, cyano, $(C_1-C_3)$-alkyl, $(C_1-C_3)$-haloalkyl, $(C_1-C_3)$-alkoxy, hydroxy, $(C_1-C_3)$-haloalkoxy, amino, mono-$(C_1-C_3)$-alkylamino, di-$(C_1-C_3)$-alkylamino, amino-$(C_1-C_3)$-alkyl, mono-$(C_1-C_3)$-alkylamino-$(C_1-C_3)$-alkyl, di-$(C_1-C_3)$-alkylamino-$(C_1-C_3)$-alkyl, nitro or 3,5-dimethyl-1H-pyrazol-1-yl group; or $R_5$ and $R_6$ when taken together with two carbon atoms to which they are attached form a five-membered heterocyclic radical 2,5-dihydrofuranyl of the following formula:

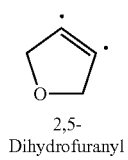

2,5-Dihydrofuranyl

In a particular embodiment, the present invention further provides inhibitors of methionine metabolic pathway having the Formula (IA1), wherein Q is C—$R_7$;

$R_3$ is pyridinyl or phenyl substituted at any available aromatic ring carbon atom with one or two groups, wherein the first group is optional and selected from carboxylmethyl and carboxyl group, and the second is the following radical:

and $R_5$ is hydrogen, halogen, cyano, $(C_1-C_3)$-alkyl, $(C_1-C_3)$-haloalkyl, $(C_1-C_3)$-alkoxy, hydroxy, $(C_1-C_3)$-haloalkoxy, amino, mono-$(C_1-C_3)$-alkylamino, di-$(C_1-C_3)$-alkylamino, amino-$(C_1-C_3)$-alkyl, mono-$(C_1-C_3)$-alkylamino-$(C_1-C_3)$-alkyl, di-$(C_1-C_3)$-alkylamino-$(C_1-C_3)$-alkyl, nitro or 3,5-dimethyl-1H-pyrazol-1-yl group.

In another particular embodiment, the present invention further provides inhibitors of methionine metabolic pathway having the Formula (IA1), wherein $R_4$, $R_5$, $R_6$ and $R_7$ are independently selected from hydrogen, halogen, hydroxy, methoxy or trifluoromethyl;

$R_8$ is hydrogen, ethyl, cyclopentyl, trifluoromethyl, hydroxy, benzyl or phenylamino, wherein said benzyl or phenylamino are optionally substituted with one to three substituents independently selected from halogen, methyl, trifluoromethyl, hydroxy, methoxy or carboxylic acid group; and $R_9$ is hydrogen, methyl, ethyl, carboxymethyl or benzyl group.

The exemplary compounds of Formula (IA1) are listed below:

IML-219

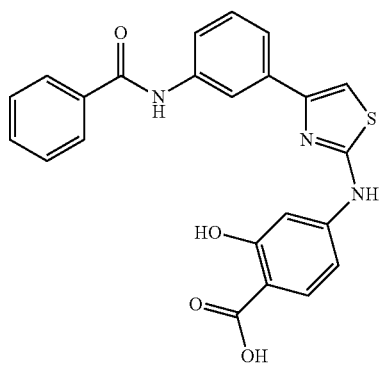

IML-213

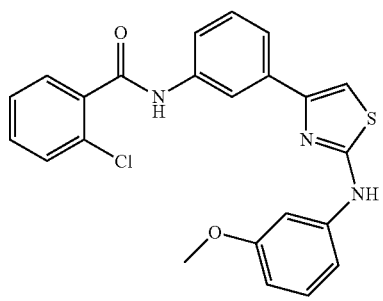

IML-215

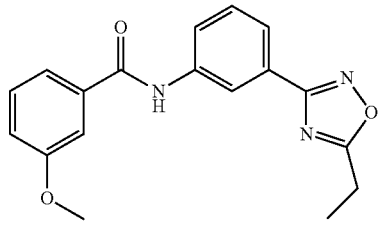

IML-222

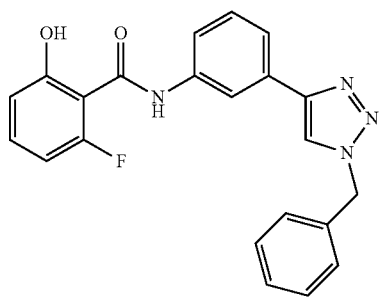

IML-220

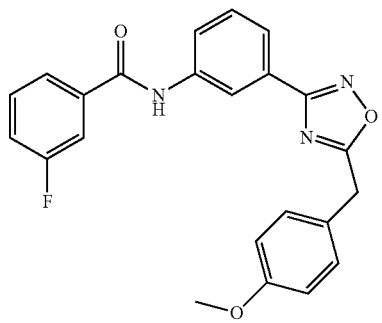

-continued
IML-212
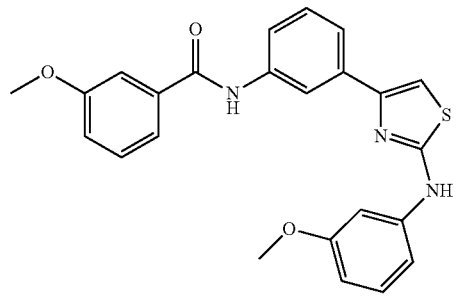
IML-214
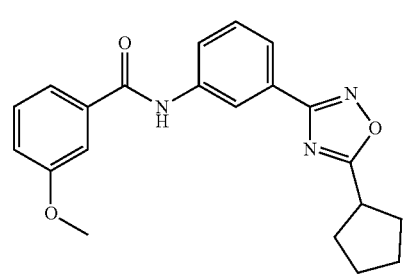
IML-211
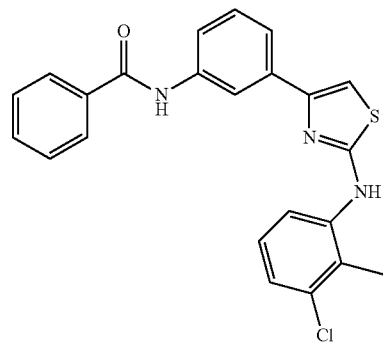
IML-217
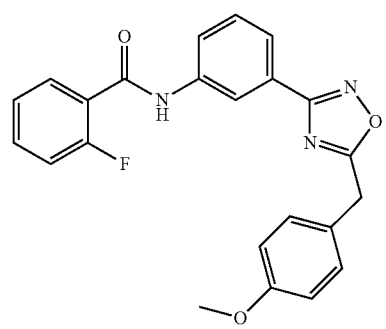
IML-69
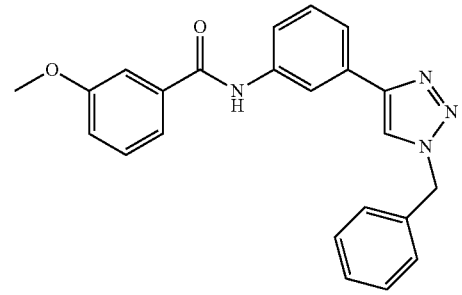
-continued
IML-225
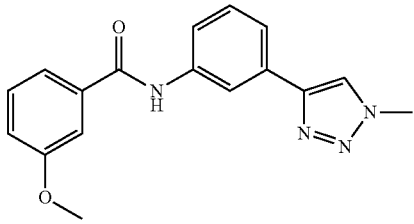
IML-70
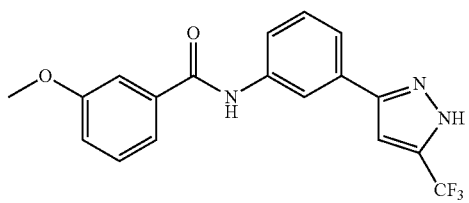
IML-71
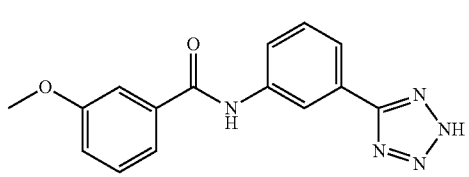
IML-229
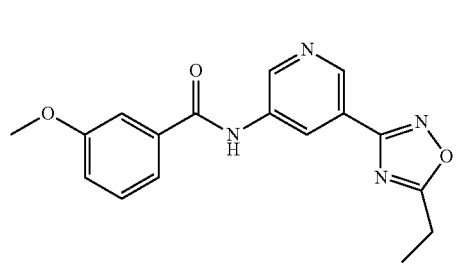
IML-230
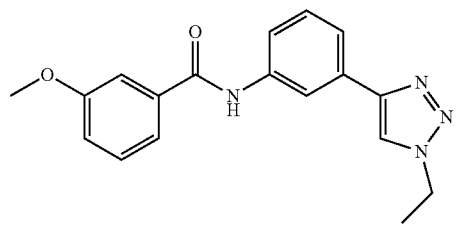
IML-231
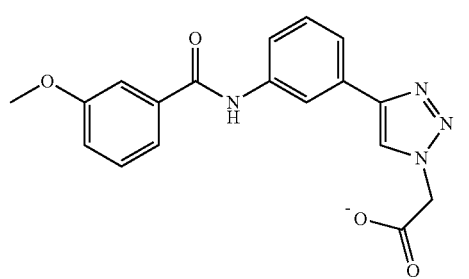

-continued

IML-234

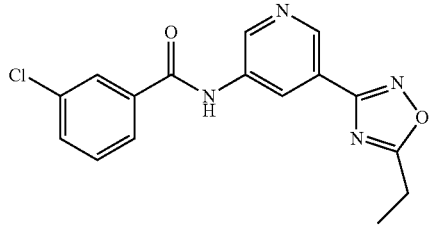

IML-235

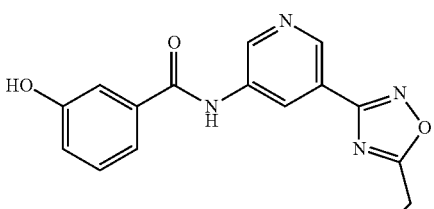

IML-228

IML-232

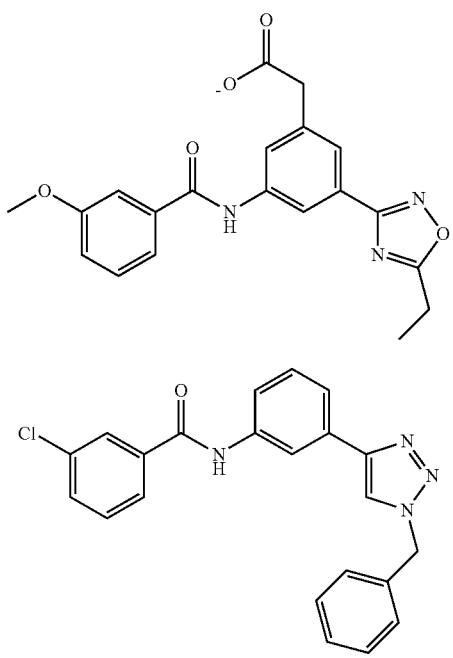

The present invention further provides inhibitors of methionine metabolic pathway having Formula (IA1), wherein Q is N;

$R_3$ is phenyl substituted at any available aromatic ring carbon atom with the following radical:

and $R_5$ is hydrogen, halogen, cyano, $(C_1-C_3)$-alkyl, $(C_1-C_3)$-haloalkyl, $(C_1-C_3)$-alkoxy, hydroxy, $(C_1-C_3)$-haloalkoxy, amino, mono-$(C_1-C_3)$-alkylamino, di-$(C_1-C_3)$-alkylamino, amino-$(C_1-C_3)$-alkyl, mono-$(C_1-C_3)$-alkylamino-$(C_1-C_3)$-alkyl, di-$(C_1-C_3)$-alkylamino-$(C_1-C_3)$-alkyl, nitro or 3,5-dimethyl-1H-pyrazol-1-yl group.

In a particular embodiment, the present invention further provides the above inhibitors of methionine metabolic pathway having the Formula (IA1), wherein Q is N, $R_4$, $R_5$ and $R_6$ are independently selected from hydrogen, halogen, methoxy or trifluoromethyl;

X and Y are independently CH or N;

Z is C—$R_8$ or N;

$R_8$ is hydrogen, ethyl, cyclopentyl, trifluoromethyl, hydroxy, benzyl or phenylamino, wherein said benzyl or phenylamino are optionally substituted with one to three substituents independently selected from halogen, methyl, trufluoromethyl, hydroxy, methoxy or carboxylic acid group;

L is N—$R_9$, O or S; and $R_9$ is hydrogen, methyl, or benzyl group.

The exemplary compounds of Formula (IA1), where in Q is N, are listed below:

IML-223

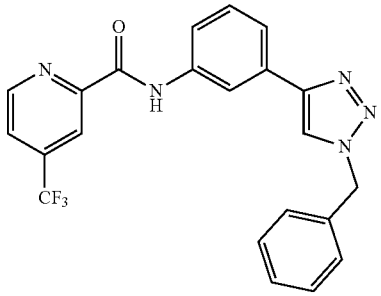

IML-224

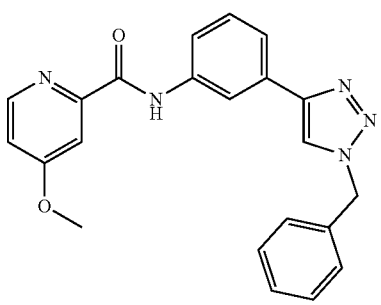

The present invention yet further provides inhibitors of methionine metabolic pathway having Formula (IA1), wherein Q is C—$R_7$;

$R_3$ is phenyl substituted at any available aromatic ring carbon atom with one group selected from the following radicals:

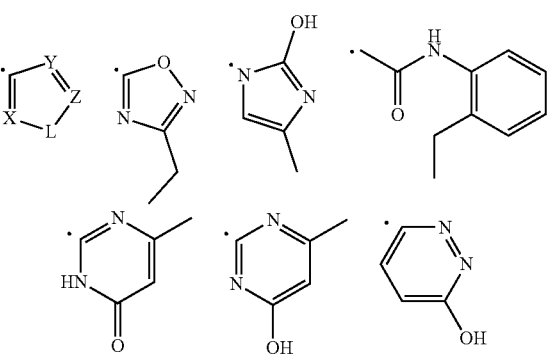

$R_4$ and $R_7$ are H; and $R_5$ and $R_6$ when taken together with two carbon atoms to which they are attached form a five-membered heterocyclic radical 2,5-dihydrofuranyl of the following formula:

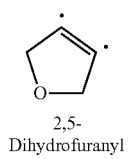

2,5-Dihydrofuranyl

The specific embodiment of the compounds having Formula (IA1), wherein Q is C—R$_7$, are the compounds having Formula (IA-13):

(IA-13)

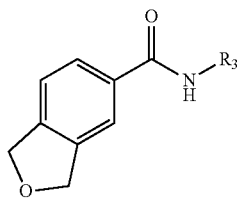

wherein R$_3$ is phenyl substituted at any available aromatic ring carbon atom with one group selected from the following radicals:

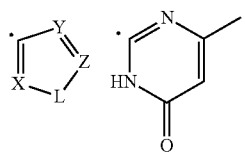

X and Y are independently CH or N;
Z is C—R$_8$ or N;
R$_8$ is hydrogen, ethyl, cyclopentyl, trifluoromethyl, hydroxy, benzyl or phenylamino, wherein said benzyl or phenylamino are optionally substituted with one to three substituents independently selected from halogen, methyl, trufluoromethyl, hydroxy, methoxy or carboxylic acid group;
L is N—R$_9$, O or S; and
R$_9$ is hydrogen, methyl, or benzyl group.
The exemplary compounds of Formula (IA-13) are listed below:

IML-221

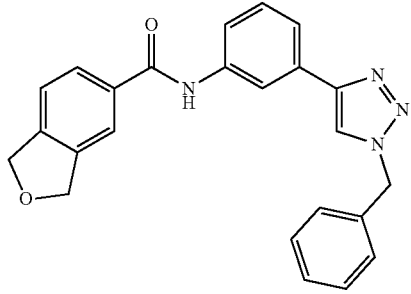

IMS-13 (74)

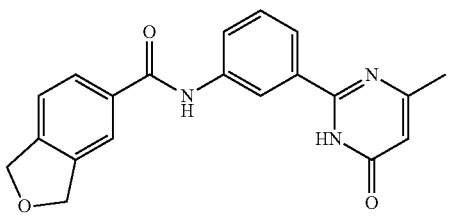

In another embodiment, the present invention further provides inhibitors of methionine metabolic pathway having Formula (I), wherein Q is C—R$_7$;
R$_3$ is phenyl substituted at any available aromatic ring carbon atom with one group selected from the following radicals:

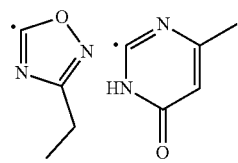

and R$_5$ is hydrogen, halogen, cyano, (C$_1$-C$_3$)-alkyl, (C$_1$-C$_3$)-haloalkyl, (C$_1$-C$_3$)-alkoxy, hydroxy, (C$_1$-C$_3$)-haloalkoxy, amino, mono-(C$_1$-C$_3$)-alkylamino, di-(C$_1$-C$_3$)-alkylamino, amino-(C$_1$-C$_3$)-alkyl, mono-(C$_1$-C$_3$)-alkylamino-(C$_1$-C$_3$)-alkyl, di-(C$_1$-C$_3$)-alkylamino-(C$_1$-C$_3$)-alkyl, nitro or 3,5-dimethyl-1H-pyrazol-1-yl group.

In a specific embodiment, these compounds of Formula (I), having Q defined as C—R$_7$ and R$_3$ and R$_5$ as defined above, have R$_4$, R$_6$ and R$_7$ independently selected from hydrogen, ethyl, halogen, hydroxy, methoxy, trifluoromethyl, difluoromethoxy, amino, dimethylamino and dimethylamino-methyl; and R$_5$ is hydrogen, halogen, ethyl, trifluoromethyl, amino, dimethylamino, hydroxy, methoxy or 3,5-dimethyl-1H-pyrazol-1-yl group. The exemplary compounds of this embodiment are listed below:

IML-10 (72)

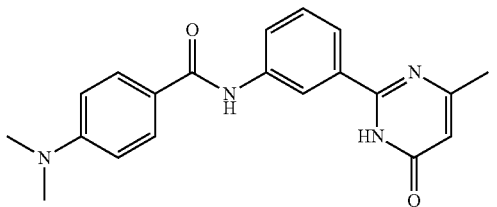

IML-25

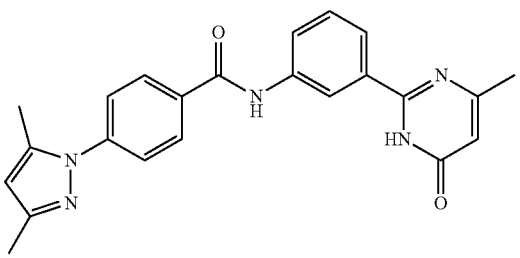

IML-11 (73)

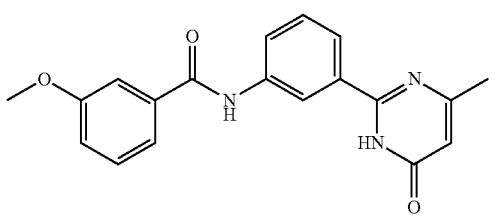

-continued

IML-26
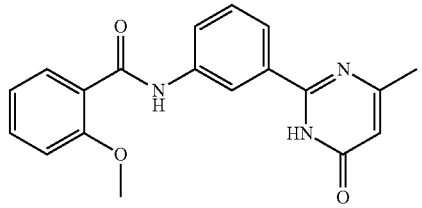

IML-12
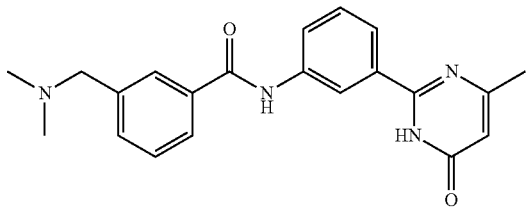

IML-14
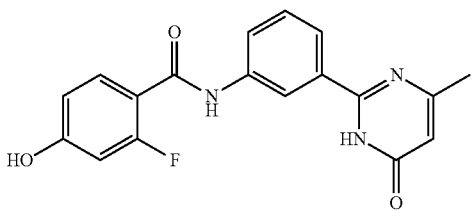

IML-16
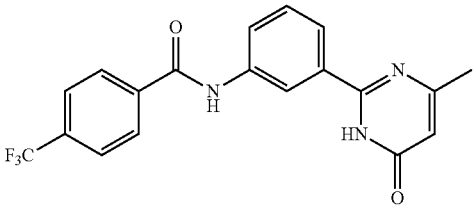

IML-22
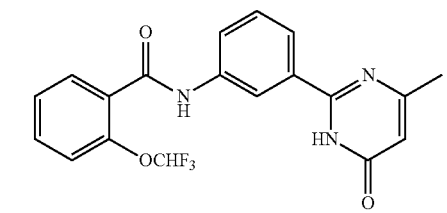

IML-23
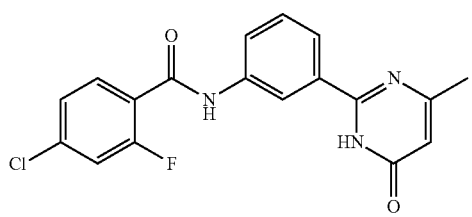

IML-24
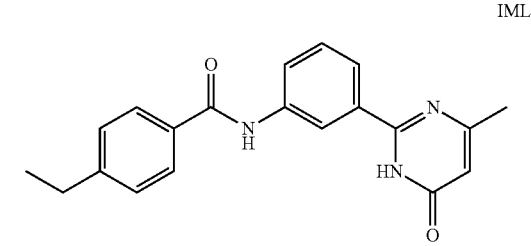

-continued

IML-15
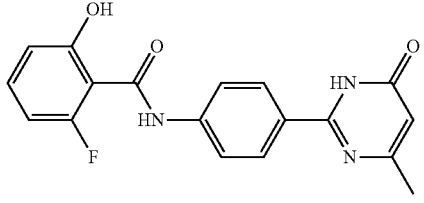

IML-216
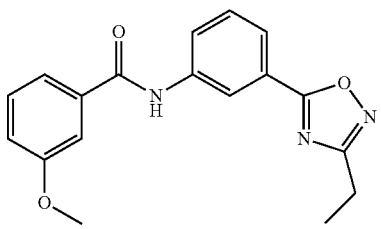

The present invention also provides the inhibitors of methionine metabolic pathway having the Formula (IA1), wherein Q is C—$R_7$ or N;

$R_3$ is phenyl substituted at any available aromatic ring carbon atom with one group selected from the following radicals:

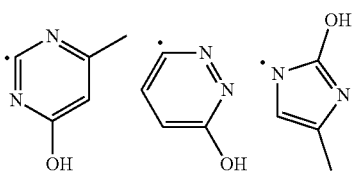

and $R_5$ is hydrogen, halogen, cyano, ($C_1$-$C_3$)-alkyl, ($C_1$-$C_3$)-haloalkyl, ($C_1$-$C_3$)-alkoxy, hydroxy, ($C_1$-$C_3$)-haloalkoxy, amino, mono-($C_1$-$C_3$)-alkylamino, di-($C_1$-$C_3$)-alkylamino, amino-($C_1$-$C_3$)-alkyl, mono-($C_1$-$C_3$)-alkylamino-($C_1$-$C_3$)-alkyl, di-($C_1$-$C_3$)-alkylamino-($C_1$-$C_3$)-alkyl, nitro or 3,5-dimethyl-1H-pyrazol-1-yl group.

In a specific embodiment, these compounds of Formula (IA1), having Q defined as C—$R_7$, and $R_3$ and $R_5$ as defined above, have $R_4$, $R_5$, $R_6$ and $R_7$ independently selected from hydrogen, halogen, amino, hydroxy or methoxy. The exemplary compounds of this embodiment are listed below:

IMS-202 (9)
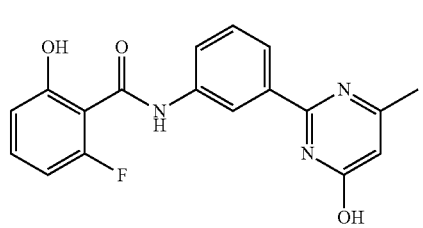

IML-67
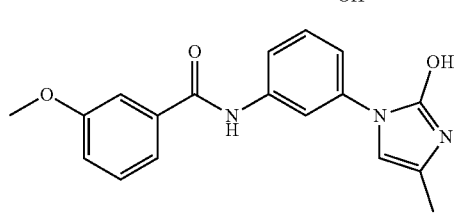

-continued

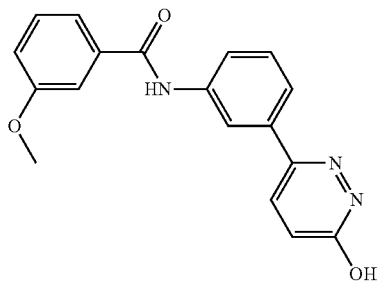

IML-68

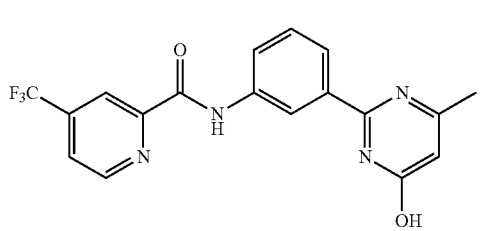

IML-65

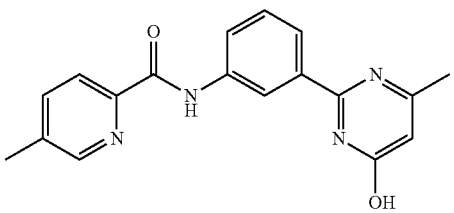

IML-66

The present invention further provides the inhibitors of methionine metabolic pathway having the Formula (IA1), wherein Q is N, and $R_3$ is phenyl substituted at any available aromatic ring carbon atom with the following radical:

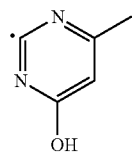

In a specific embodiment, these compounds of Formula (IA1), having Q defined as N, and $R_3$ as defined above, have $R_4$, $R_5$, and $R_6$ are independently selected from hydrogen, methyl, hydroxy, methoxy or trifluoromethyl. The exemplary compounds of this embodiment are listed below:

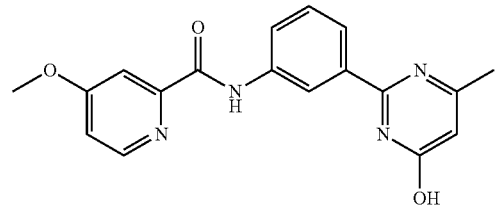

IML-62

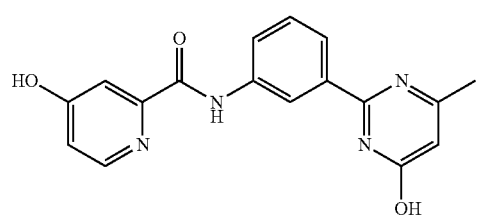

IML-63

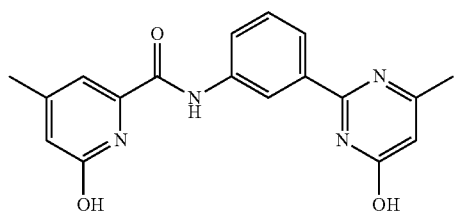

IML-64

The present invention further provides the inhibitors of methionine metabolic pathway having Formula (IA-2):

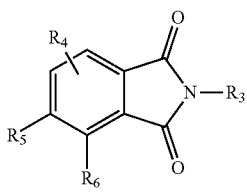

(IA-2)

wherein $R_3$ is phenyl substituted at any available aromatic ring carbon atom with the following radical:

In a particular embodiment, the compounds of the Formula (IA-2) as defined above, have the groups X defined as CH, Y as N, Z as C—$R_8$, where $R_8$ is phenylamino group optionally substituted with one to three substituents independently selected from halogen, ($C_1$-$C_3$)-alkyl, ($C_3$-$C_6$)-cycloalkyl, ($C_1$-$C_3$)-haloalkyl, hydroxy, ($C_1$-$C_3$)-alkoxy, carboxylic acid, cyano, amino and nitro group. The exemplary compound of this embodiment is:

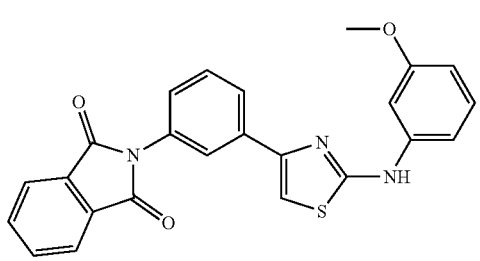

IML-218

Other exemplary compounds of Formula (I) of the present inventions are:

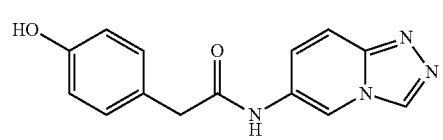
IML-50

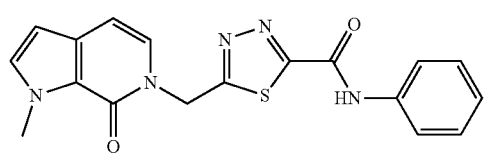
IML-29

The present invention further provides the inhibitors of methionine metabolic pathway having Formula (ID):

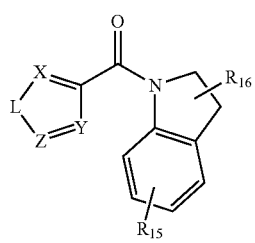
(ID)

wherein $R_{15}$ and $R_{16}$ are independently selected from hydrogen, halogen, nitro, carboxylic acid, carboxylate, acetic acid and acetate group.

In a particular embodiment, the compounds of Formula (ID) have Z defined as C—$R_8$ or N, $R_8$ as hydrogen, and L as N—$R_9$, wherein $R_9$ is phenyl optionally substituted with one to three halogen atoms; $R_{15}$ is selected from hydrogen, halogen, nitro and carboxylic acid group; and $R_{16}$ is hydrogen atom or carboxylic acid group. The exemplary compounds of this embodiment are listed below:

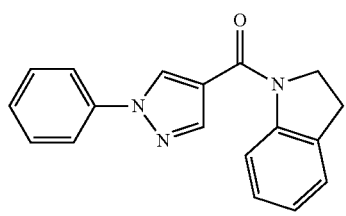
IML-30

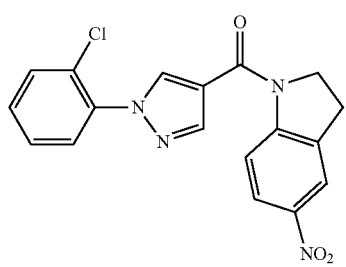
IML-33

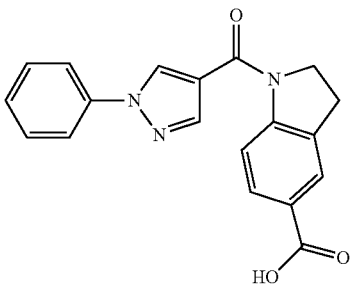
IML-31

IMS-198 (7)

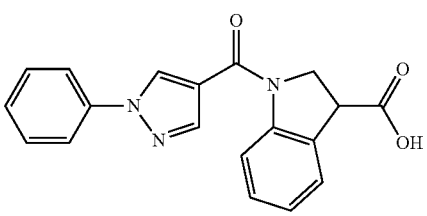
IML-32

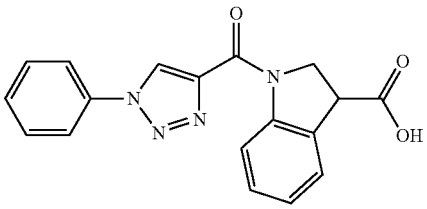
IML-162

IML-120

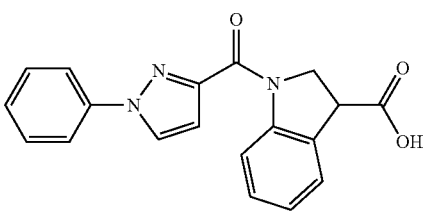
IML-121

IML253

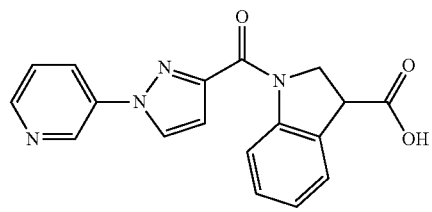

In a particular embodiment, the compounds of Formula (ID) have X defined as CH, Y as N, L as N—$R_9$ or O, $R_9$ as hydrogen, Z as C—$R_8$, wherein $R_8$ is pyridinyl or phenyl, wherein said phenyl is optionally substituted with one to three same or different substituents at any available aromatic ring carbon atom, said substituents are selected from halogen, hydroxy and methoxy group, $R_{15}$ is selected from hydrogen, halogen, nitro and carboxylic acid group, and $R_{16}$ is selected from hydrogen, carboxylic acid and acetic acid group. The exemplary compounds of this embodiment are listed below:

IML-124

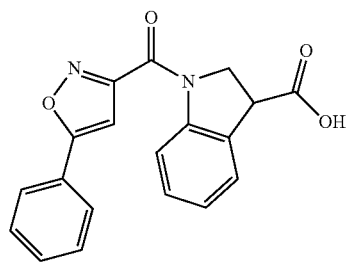

IML-164

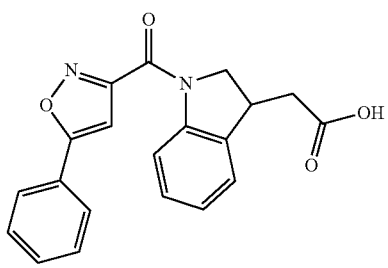

IML-183

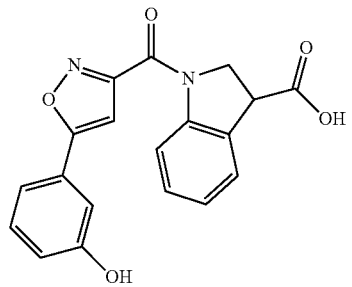

IML-184

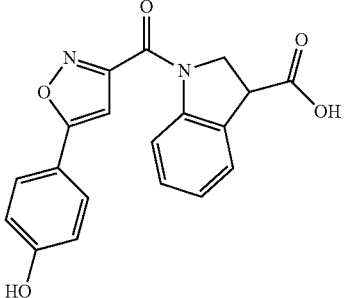

IML-180

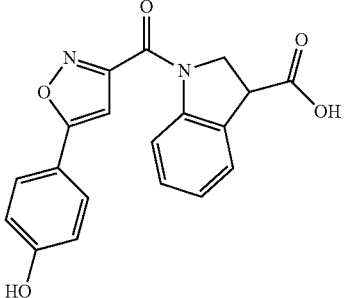

IML-161

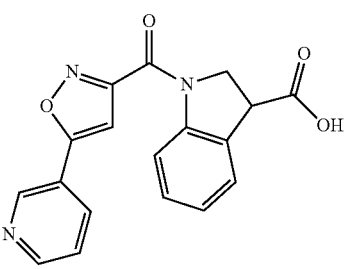

IML-166

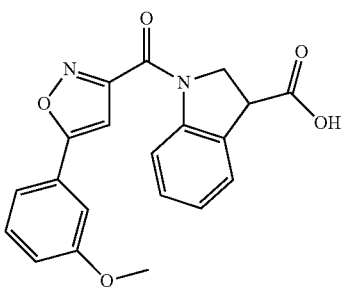

IML-181

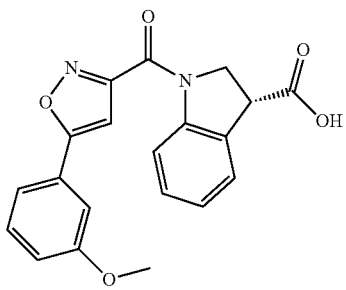

IML-238

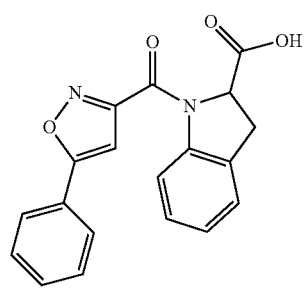

IML-163

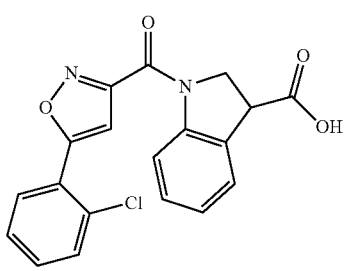

IML-167

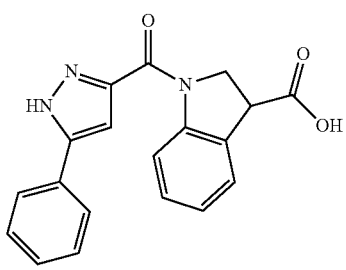

IML-125

The present invention further provides the inhibitors of methionine metabolic pathway having Formula (IE):

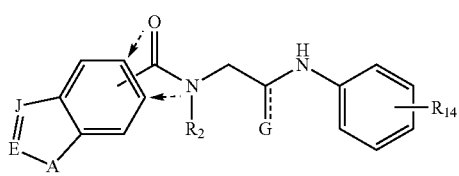

(IE)

wherein two dashed arrows points to two carbon atoms of the phenyl ring, to which the carbonyl can be attached, $R_2$ is hydrogen or $(C_1-C_3)$-alkyl;

$R_{14}$ is one to three same or different substituents attached to any available carbon atom of the phenyl ring and independently selected from hydrogen, amino, $(C_1-C_3)$-alkyl, $(C_1-C_3)$-haloalkyl, $(C_1-C_3)$-alkoxy, $(C_1-C_3)$-alkylcarboxylic acid, carboxylic acid, $(C_1-C_3)$-alkylcarboxylate, carboxylate, $(C_1-C_3)$-alkylcarboxamide, carboxamide, halogen, cyano, hydroxy, nitro and acetylamino group;

A is CH—$R_{10}$ or N—$R_{11}$;

E is C—$R_{12}$ or N;

J is C—$R_{13}$ or N;

$R_{10}$, $R_{11}$, $R_{12}$, and $R_{13}$ are independently selected from hydrogen, $(C_1-C_3)$-alkyl and $(C_1-C_3)$-haloalkyl; and either:

===== is a double bond, and G is O; or

===== is a single bond, and G taken together with the two adjacent carbon atoms and with the nitrogen atom to which the second carbon atom is attached forms a five- or six-membered heterocyclic ring.

In one particular embodiment, the compounds of Formula (IE) have ===== defined as a double bond and G as oxygen atom, wherein $R_{14}$ is one substituent attached to any available carbon atom of the phenyl ring and selected from hydrogen, $(C_1-C_3)$-alkyl and acetylamino group, and $R_{10}$, $R_{11}$, $R_{12}$, and $R_{13}$ are independently selected from hydrogen and $(C_1-C_3)$-alkyl. The exemplary compounds of this embodiment are listed below:

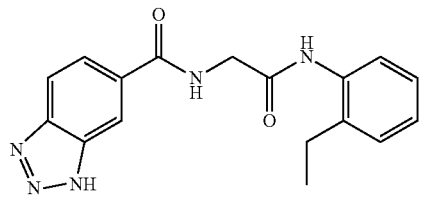 [SMILES: CCc1ccccc1NC(=O)CNC(=O)c1ccc2nn[nH]c2c1]

IML-102

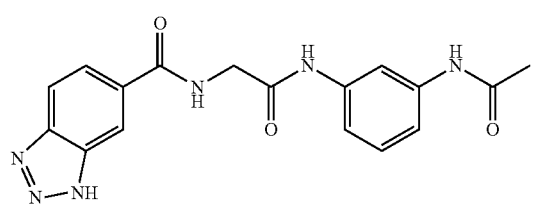 [SMILES: CC(=O)Nc1cccc(NC(=O)CNC(=O)c2ccc3nn[nH]c3c2)c1]

IML-110

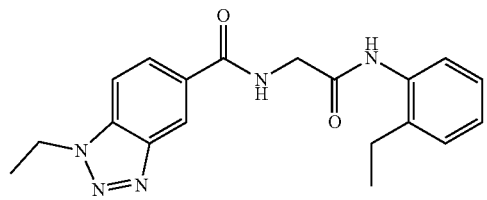 [SMILES: CCc1ccccc1NC(=O)CNC(=O)c1ccc2c(c1)nnn2CC]

IML-112

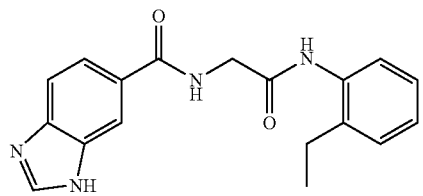

IML-113

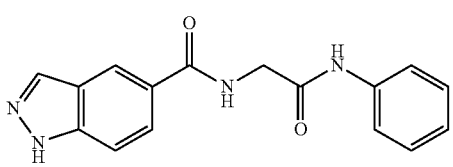

IML-134

IML-183

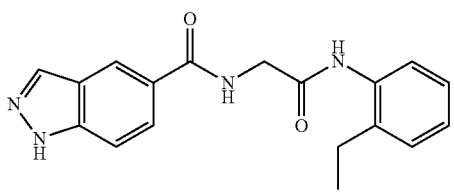

In another particular embodiment, the compounds of Formula (IE) have ==== defined as a single bond, and G taken together with the two adjacent carbon atoms and with the nitrogen atom, to which the second carbon atom is attached, forms a five- or six-membered heterocyclic ring, wherein $R_{14}$ is one substituent attached to any available carbon atom of the phenyl ring and selected from hydrogen, $(C_1$-$C_3)$-alkyl and acetylamino group, and $R_{10}$, $R_{11}$, $R_{12}$, and $R_{13}$ are independently selected from hydrogen and $(C_1$-$C_3)$-alkyl. The exemplary compounds of this embodiment are listed below:

IML-203

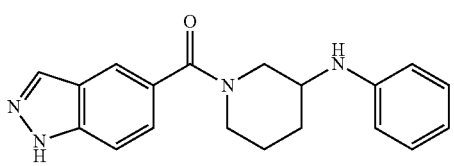

IML-204

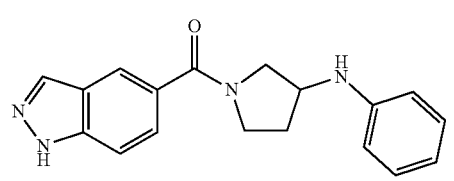

The compounds of the present invention can be used as herbicides, pesticides, fungicides, agricultural plant stimulants or antimicrobial agents. The compounds of the present invention can be used for seed treatment. In a particular embodiment, the compounds of the present invention are used as selective herbicides, non-selective herbicides, agricultural herbicides, non-agricultural herbicides, herbicides in integrated pest management, herbicides in gardening, herbicides in clearing waste ground, herbicides in clearing industrial or constructions sites, or herbicides in clearing railways and railway embankments.

As will be demonstrated below, the compounds of the present invention are indeed herbicidally active and would be effective in regulating growth of a wide variety of undesirable plants, i.e., weeds, when applied, in herbicially effective amount, to the growth medium prior to emergence of the weeds or to the weeds subsequent to emergence from the growth medium. The term "herbicidally effective amount" is that amount of a compound or mixture of compounds of the present invention required to so injure or damage weeds such that the weeds are incapable of recovering following application. The quantity of a compound or mixture of compounds of the present invention applied in order to exhibit a satisfactory herbicidal effect may vary over a wide range and depends on a variety of factors, such as, for example, hardiness of a particular weed species, extent of weed infestation, climatic conditions, soil conditions, method of application and the like. Of course, the efficacy of a particular compound against a particular weed species may readily be determined by routine laboratory or field testing in a manner well known to the art.

A compound or compounds of the present invention can be used in various formulations with agronomically acceptable adjuvants, inert carriers, other herbicides, or other commonly used agricultural compounds, for example, insecticides, fungicides, pesticides, stabilisers, safeners, fertilisers or the like. The compounds of the present invention alone or in formulation with other agronomically used materials are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to about 95 percent by weight on weight of the formulation. Typically, such formulations would contain from about 5 to 75 percent by weight of a compound or compounds of the present invention.

Weeds that may be effectively controlled by the application of compounds of the present invention are for example, barnyard grass (*Echinochloa crusgalli*), crabgrass (*Digitaria sanguinalis*), rockcress (*Arabidopsis thaliana*), coffee weed (*Daubentonia* punices), jimsonweed (*Datura* stamonium), Johnson grass (*Sorghum halepense*), tall morning glory (*Ipomoea purpurea*), wild mustard (*Brassica* caber), tea weed (*Sida Spinosa*), velvetleaf (*Abutilon Theophrasti*), wild oat (*Avena fatua*), yellow foxtail (*Setaria glauca*), yellow nutsedge (*Cyperus esculentus*) and the like.

As mentioned above, the compounds of the present invention are applied to the locus of the unwanted vegetation, to the undesired plants or to a habitat thereof, in a form of herbicidal compositions comprising a herbicially effective amount of the compound or compounds. As a post-emergent, the herbicides of the invention may be applied to the locus of the unwanted vegetation neat or as an emulsion or solution. Any solvent in which the herbicide is soluble or may be emulsified may be employed as a diluent. Suitable solvents include water or water-soluble alcohols, such as methanol, ethanol, and isopropyl alcohol, or a ketone such as acetone or methyl ethyl ketone. Such compounds further form emulsions with water.

In a further embodiment of the present invention, a method for the control of undesired vegetation or clearing areas from the undesired vegetation comprises applying to the locus of said undesired vegetation a herbicially effective amount of a compound or compounds of the present invention. The method of the invention may be used to control established vegetation in the vicinity of a seeded crop or in a weed concentrate area by contacting the foliage of the unwanted vegetation with the herbicidal composition. The herbicidal activity of such herbicidal compositions rapidly dissipates in the unwanted vegetation upon contact. The locus of the undesired plants treated by the compounds of the present invention may be agricultural areas, crop fields, gardens, waste grounds, industrial or constructions sites, railways or railway embankments.

The compounds of formula (I) have been discovered by in-silico screening method. A thorough structural analysis of the CGS protein structure (based on published X-ray structures) and identification of potential binding sites for small molecule inhibitors was performed. Virtual screening was carried out based on herbicide-like profiled library of small molecules. The profiled library was generated based on an in-house database of approximately 30 million small organic compounds taken from various commercial sources. Based on a list of all available herbicides, the chemical space of in-planta active compounds was defined. The database was filtered based on this set of unique properties, for example profiling to yield the initial set of compounds which may have the potential to be active in plants. These were used for the virtual and in-vitro screening.

There are two types of the CGS crystal structures in a complex with inhibitors available in biomolecular databases, such as PDB (Protein Data Bank). These two structures incorporate the pyridoxal phosphate co-factor (PLP):
1) Structure with the PDB code 1I41, having a covalent binder, such as the natural metabolite cysthionine; and
2) Structure with the PDB codes 1I48 and 1QGN, having non-covalent binders, which include two crystal structures of the protein active site.
Therefore, in-silico screening was performed using two types of molecular docking and three structures of the enzyme. One type of the molecular docking was aimed at the potential covalent (irreversible) binders and another one—at the reversible binders.

The expression test of the latter with coomassie-stained 12% sodium dodecyl sulphate (SDS) gel clearly demonstrated accumulation of the band after induction of the BL21-plys cells containing a plasmid with the CGS gene. The bands molecular weight fitted the anticipated protein size.

In order to test the CGS enzyme in various assays, the DNA sequence of MetB gene from *Nicotiana tabacum* that is translated to the CGS enzyme was cloned. The gene was cloned into a modified pET11 vector containing an N-terminus 6xHIS and GB1 solubility tag followed by a TEV cleavage site. In order to validate that the CGS is expressed as a soluble protein, the following expression and purification were carried out. For the protein expression test and setting up the primary screening assay, the following constructs were used:
1. CGS (*Tabacum*)-His' (pet vector)
2. GST-CGS (*Tabacum*)-His' (pgex vector)
3. CGS (Arabidobsis)-His' (pet vector)
4. GST-CGS (Arabidobsis)-His' (pgex vector)
Each of the above plasmids was tested for expression of soluble protein with two different types of *E. coli*: BL-21 and BL-21 plys. These two representative colonies of BL21 cells that were transformed with the CGS containing vector were cultured at 37° C. until optical density (OD) at 600 nm=0.8 was achieved. At this point, 1 mM IPTG was added and the cells were further cultured for additional four hours. The preliminary expression tests were positive for all CGS constructs.

In order to purify the CGS protein from the cellular lysate, two consecutive purification methods were used: nickel column and S75 size exclusion chromatography. The nickel column binds the HISx6 tag expressed C-terminus to the CGS. The content of the soluble fraction of the first colony was passed through the nickel column and the eluted fractions were run on a coomassie-stained 12% sodium dodecyl sulphate (SDS) gel electrophoresis. FIG. 1 shows the coomassie-stained 12% SDS gel electrophoresis of the proteins eluted from the nickel column. The accumulation of the soluble CGS can be observed in Lanes 8 and 9 and the purified protein is marked by its clear appearance as a single band in Lane 10.

In order to verify that the purified enzyme is active, a new biochemical in-vitro activity assay was currently developed by the present inventors. This assay is utilising the chemical reaction catalysed by the CGS enzyme, which is the conversion of cysteine and phospho-serine ester into cystathionine, according to the following reaction scheme:

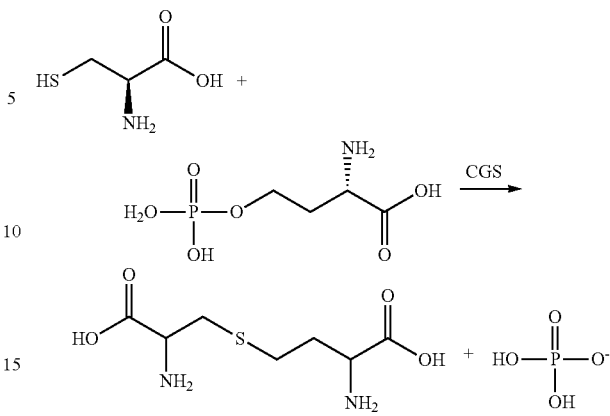

The phosphate that is released as a by-product in this reaction can then be monitored by its conjugation in the additional selective chemical reaction, the conversion of 2-amino-6-mercapto-7-methylpurine riboside (MESG) to ribose 1-phosphate and 2-amino-6-mercapto-7-methylpurine by the enzyme purine nucleoside phosphorylase (PNP). The latter product has a unique absorbance in the UV spectrum at 360 nm.

Figures 2A, 2B:
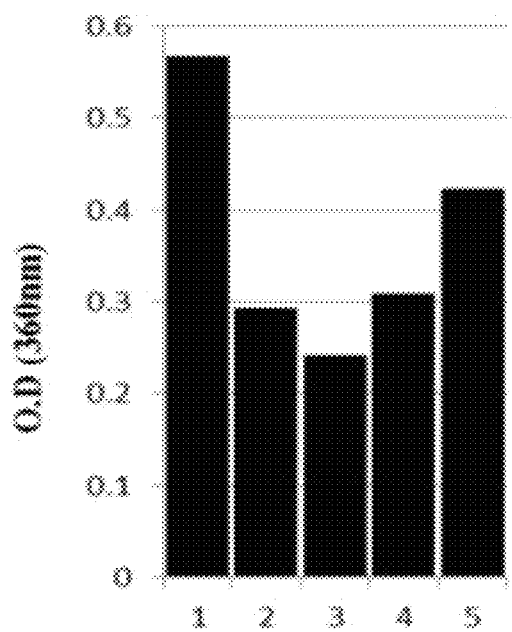
FIGS. 2a-2b show the assay development for monitoring CGS activity. The bar plots in FIG. 2a show the light absorbance at 360 nm following the incubation of CGS, cysteine and phospho-serine ester together with 7-methyl-6-thioguanosine (MESG) and purine nucleoside phosphorylase (PNP). The MESG is a chromophoric substrate used for the quantitation of inorganic phosphate in the PNP assay. The increased absorbance indicates phosphate release.
Figure 3A:
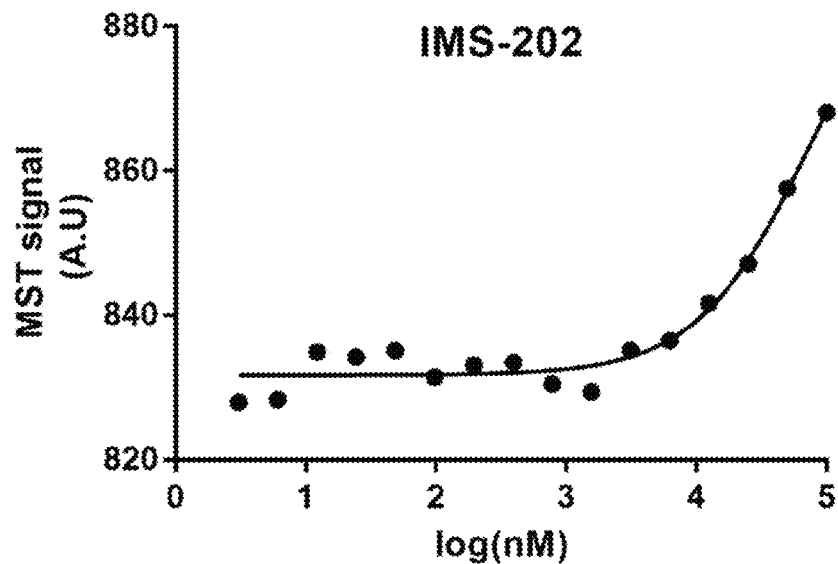
FIGS. 3a-3g show the dose-response of the compounds of the present invention with the MST full curve validation.
Figure 3B:
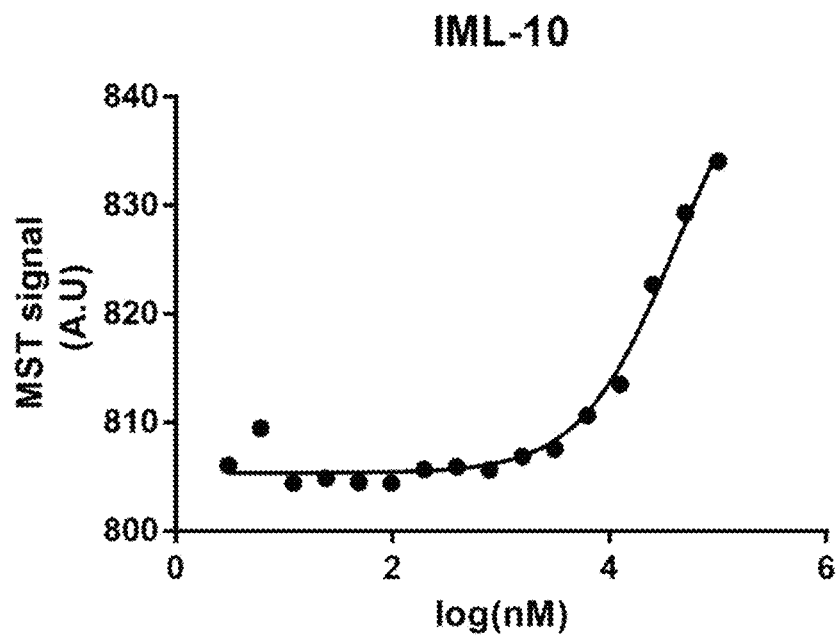
Figure 3C:
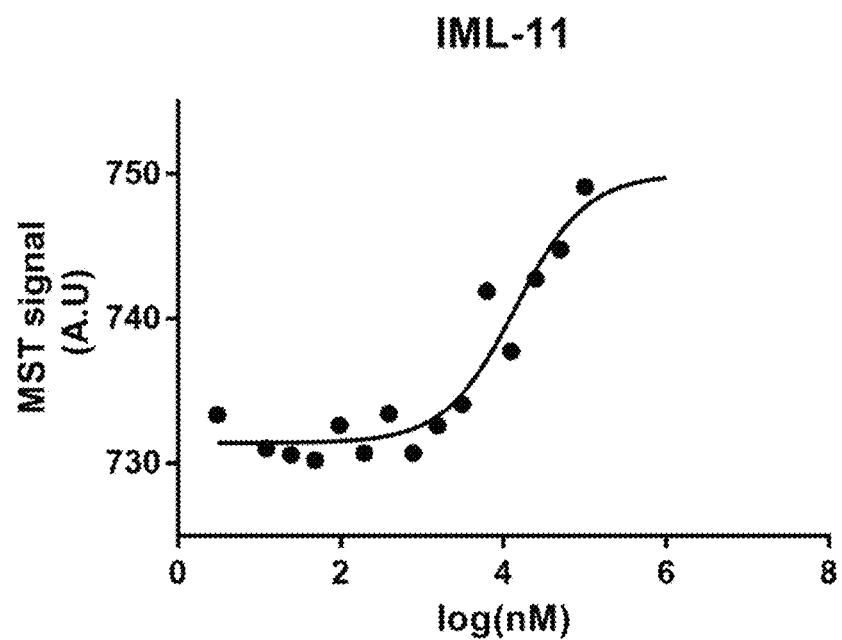
Figure 3D:
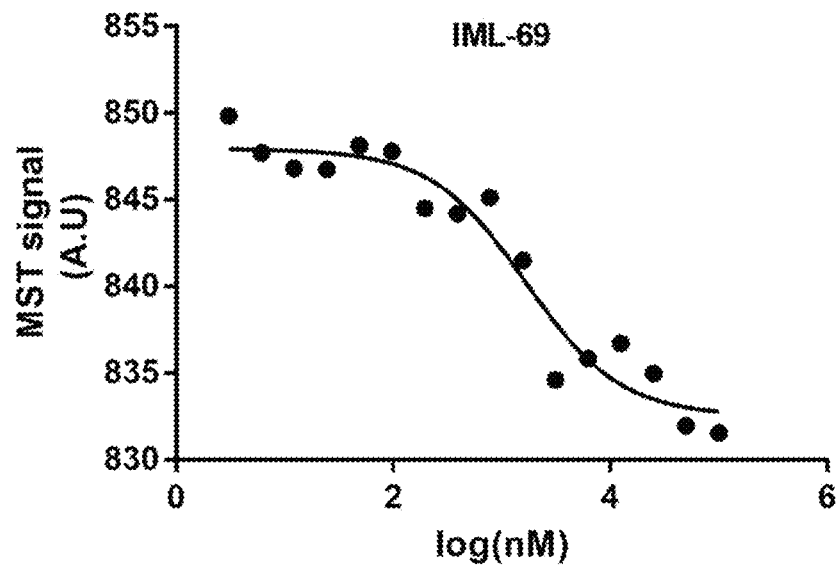
Figure 3E:
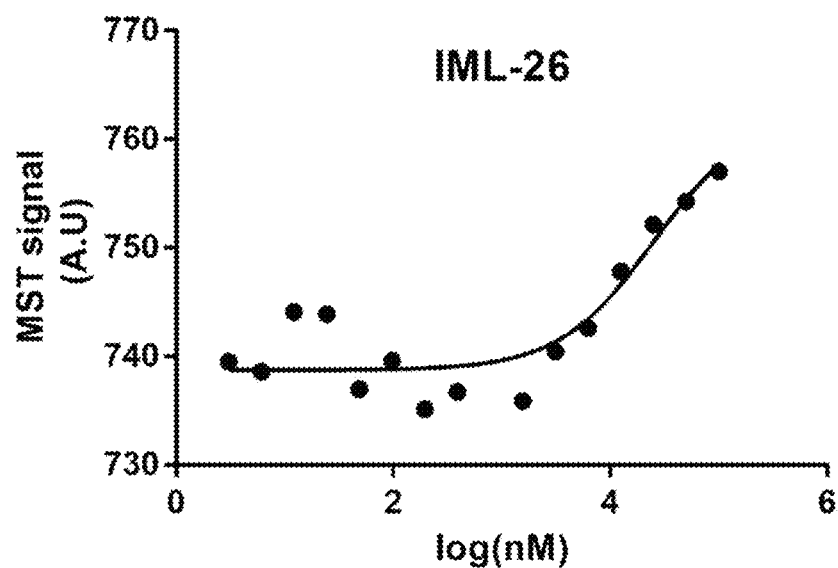
Figure 3F:
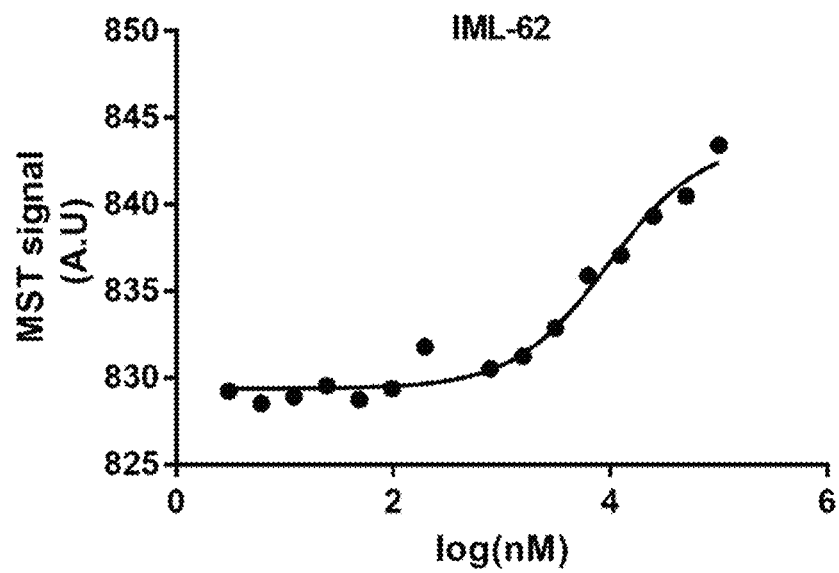
Figure 3G:
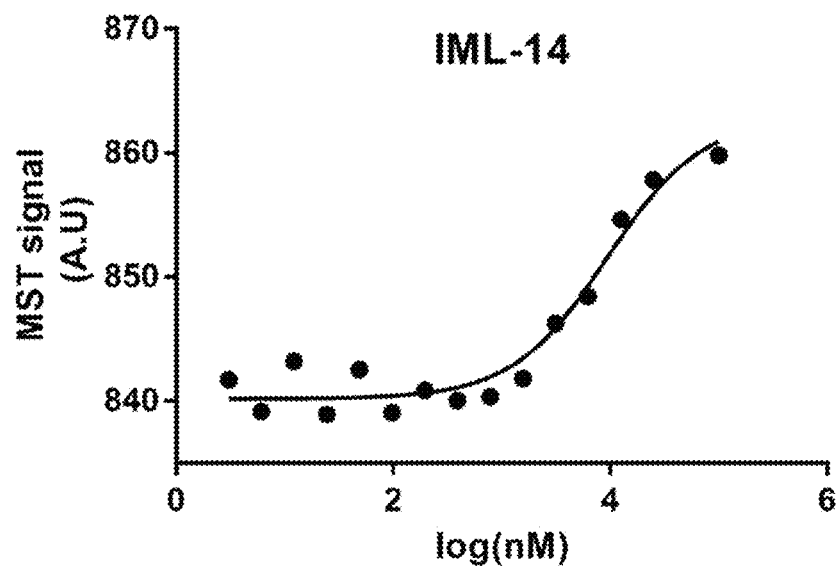

Reference is now made to FIGS. 2a-2b showing the assay development for monitoring CGS activity. The bar plots in FIG. 2a show the light absorbance at 360 nm following the incubation of CGS, cysteine and phospho-serine ester in the assay together with 7-methyl-6-thioguanosine (MESG) and purine nucleoside phosphorylase (PNP). This is a continuous spectrophotometric assay for the determination of protein phosphatase activity developed by M. R. Webb, 1992, *Proc. Natl. Acad. Sci. USA* 89, 4884-4887. The assay incorporates the coupled enzyme system with purine nucleoside phosphorylase and the chromophoric substrate 7-methyl-6-thioguanosine (MESG) used for the quantitation of inorganic phosphate. FIG. 2a shows the obtained preliminary results of the assay, which measures the light absorbance at 360 nm of the reaction mixture (Row 1). The increased light absorbance clearly indicates the phosphate release. The results where each of the initial components was removed from the mixture are shown in Rows 2-4. The results with the addition of external free phosphate are shown in Row 5. FIG. 2b presents a table showing the corresponding initial components used in the reaction.

The direct binding of the compounds of the embodiments to the CGS was tested by Micro Scale Thermophoresis (MST). In the MST assay, the CGS protein was labelled with a fluorophore, the samples were heated, and changes in fluorescence were measured as a function of the ligand concentration. In the MST assay, similar to the expression and purification described above, the recombinant Tobacco CGS protein was expressed in *E. coli* BL21 cells and purified to homogeneity. For that particular purpose, the pET-11 vector containing the DNA sequence of Tobacco CGS with an N-terminus 6xHIS tag followed by a TEV-cleavable GB1 solubility tag was cloned and transformed into the bacteria cells. Cells were cultured to OD=0.8, and protein expression was induced by the addition of 1 mM IPTG. The cells were cultured for additional 16 hours temperature 25° C.

Following cellular lysis, the soluble fraction was passed through the nickel column and the bound HIS-tagged protein was eluted by 300 mM imidazole. Then, the tags 6xHIS and GB1 were cleaved in dialysis o/n and the mixtures passed again through the nickel column to separate the CGS from the TEV and HIS-GB1 constructs. As a final step the CGS was run on S75 size exclusion chromatography.

Thus, the MST assay was performed to measure the biding of the compounds to the CGS protein. For this purpose, the CGS was labelled with commercially available amine reactive fluorophore (Cat # MO-L001, NanoTemper) according to the manufacture instructions. The MST binding curves were then measured using the Monolith NT.115 apparatus by incubating the labelled protein with the indicated compounds in a dose-response manner. As an example, FIG. 3 shows the dose-response of the compounds of the present invention with the MST full curve validation.

In addition to the direct binding evaluation, specific assay to test the compounds activity and specificity were also developed. In this assay, *E. coli* cells, lacking the endogenic MetB CGS gene and transformed to express the CGS from *Arabidopsis*, were used. These cells were grown on M9 minimal media with and without external methionine supplemented to the cells, in the presence of the compounds of the embodiments. These selected compounds of the embodiments, capable of inhibiting the cell growth on M9, but incapable of affecting the cell growth when supplemented with methionine, were validated as methionine-pathway specific inhibitors. The results of the validation experiments for a number of compounds of the present embodiments are shown in the following figures.

Figure 4A:
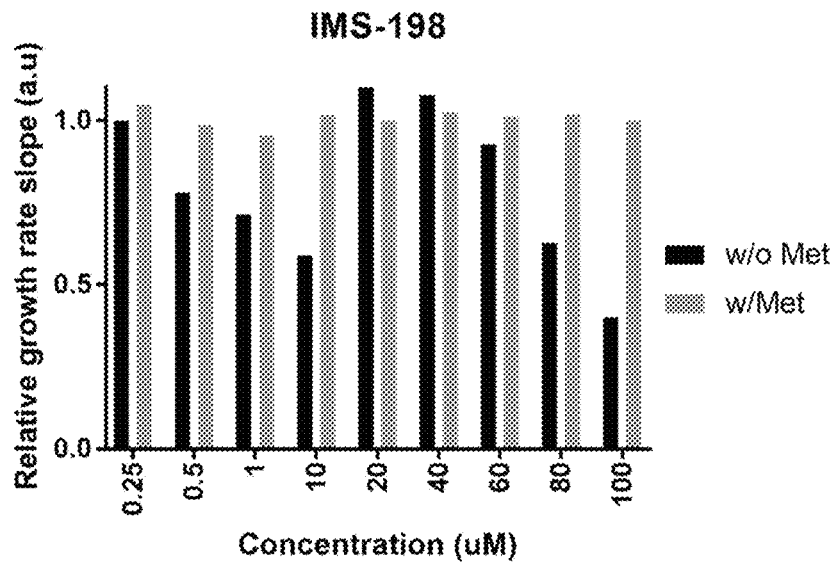
FIGS. 4a-4s demonstrate the growth rate of the engineered E. coli bacteria with the CGS gene of Arabidopsis thaliana.
Figure 4B:
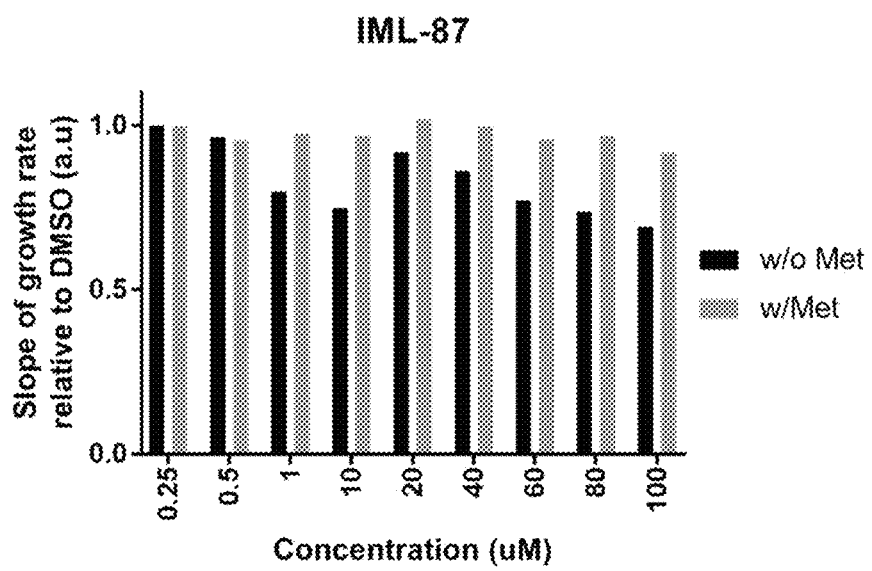
Figure 4C:
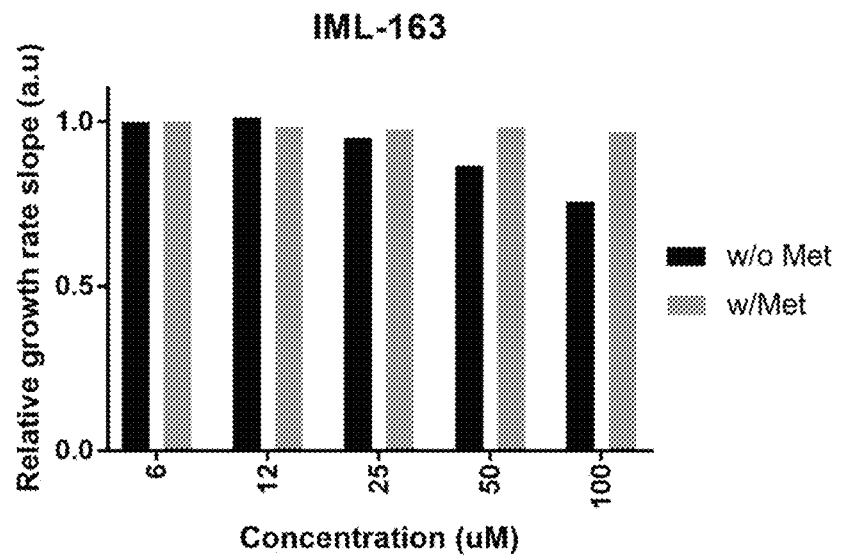
Figure 4D:
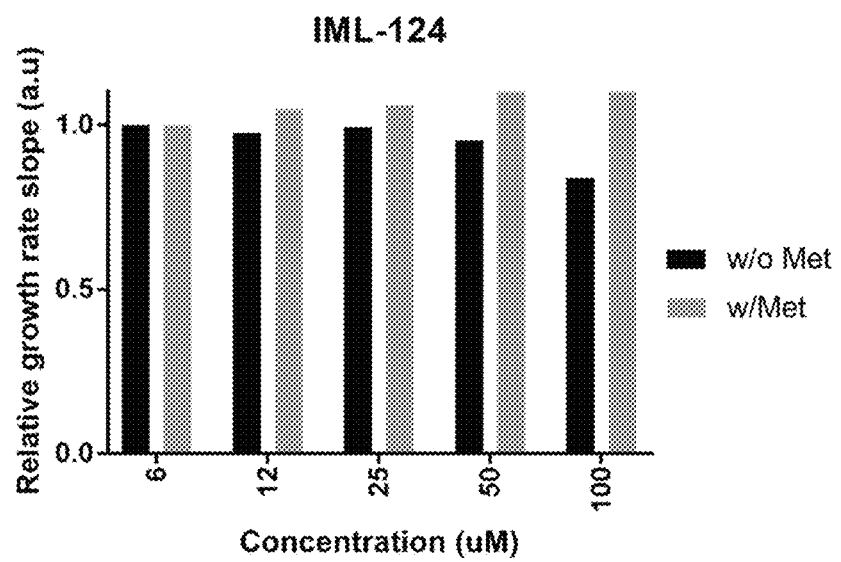
Figure 4E:
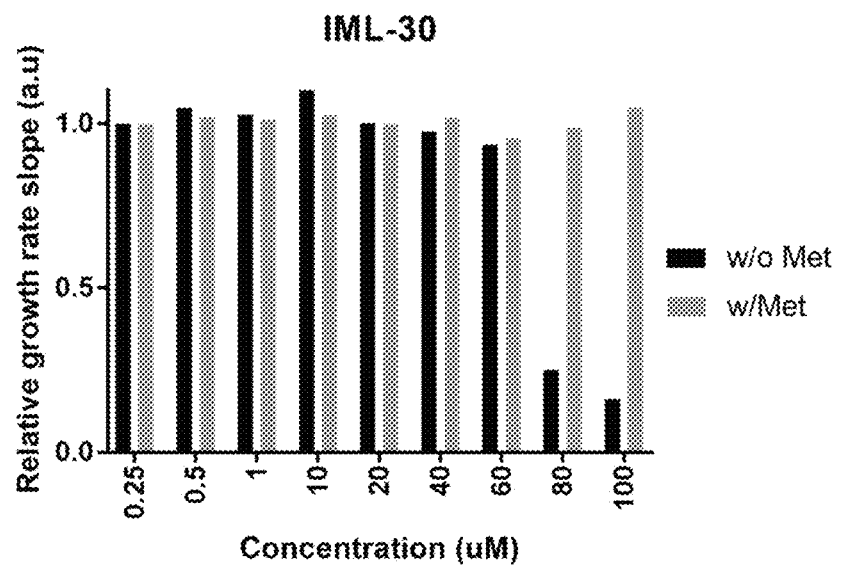
Figure 4F:
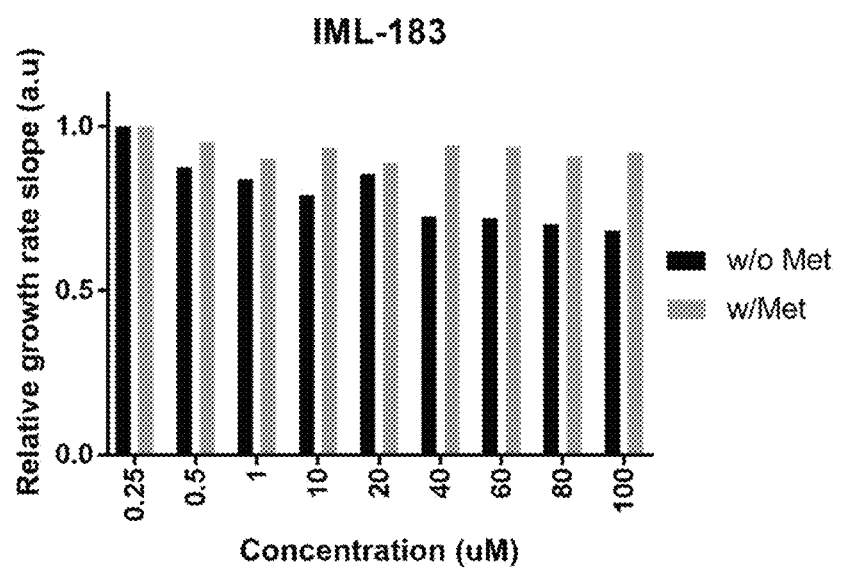
Figure 4G:
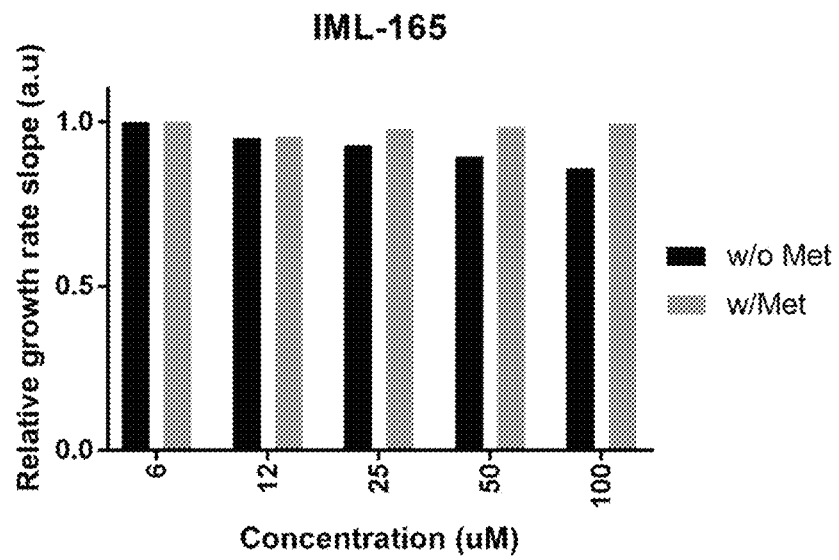
Figure 4H:
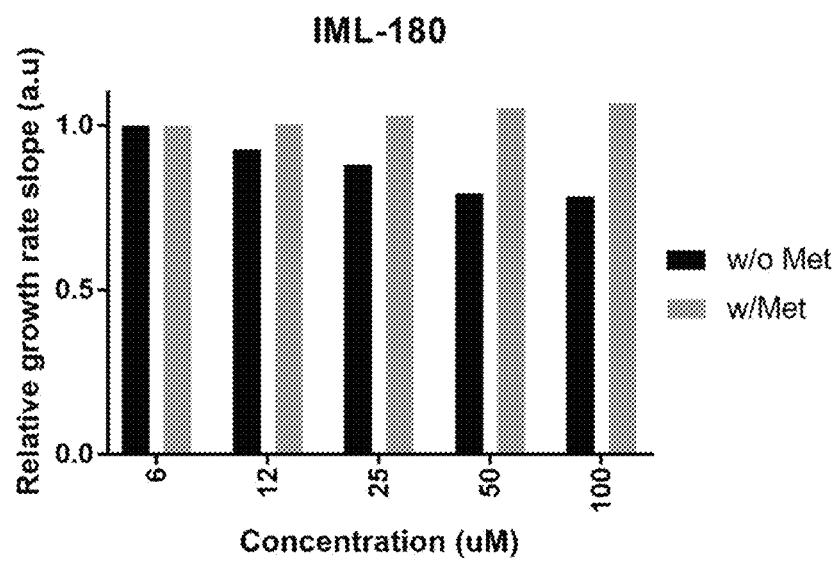
Figure 4I:
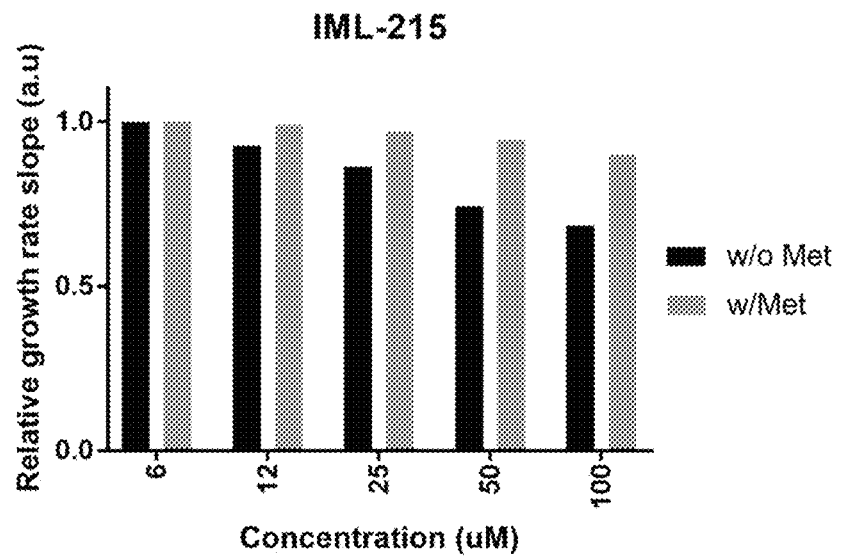
Figure 4J:
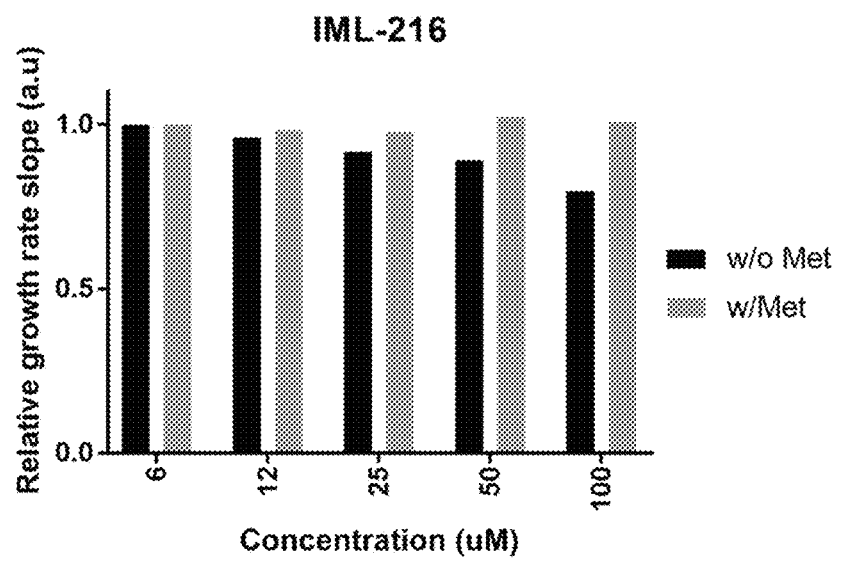
Figure 4K:
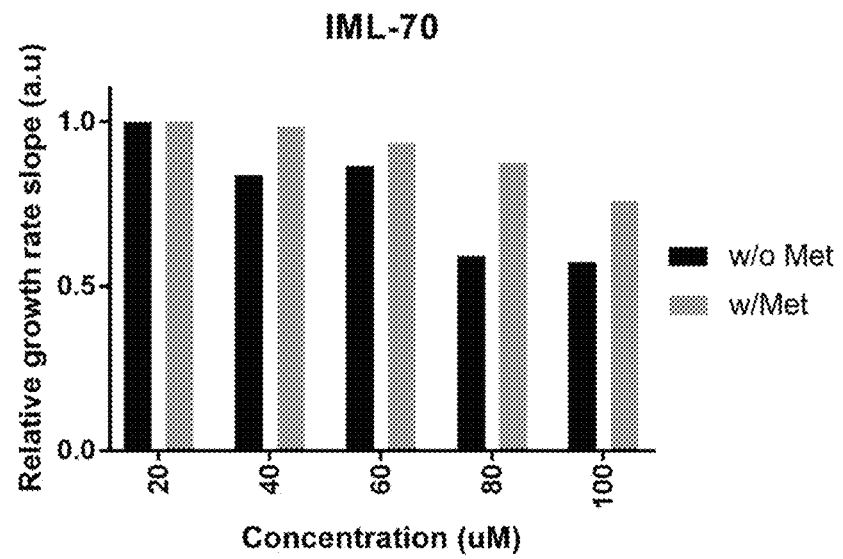
Figure 4L:
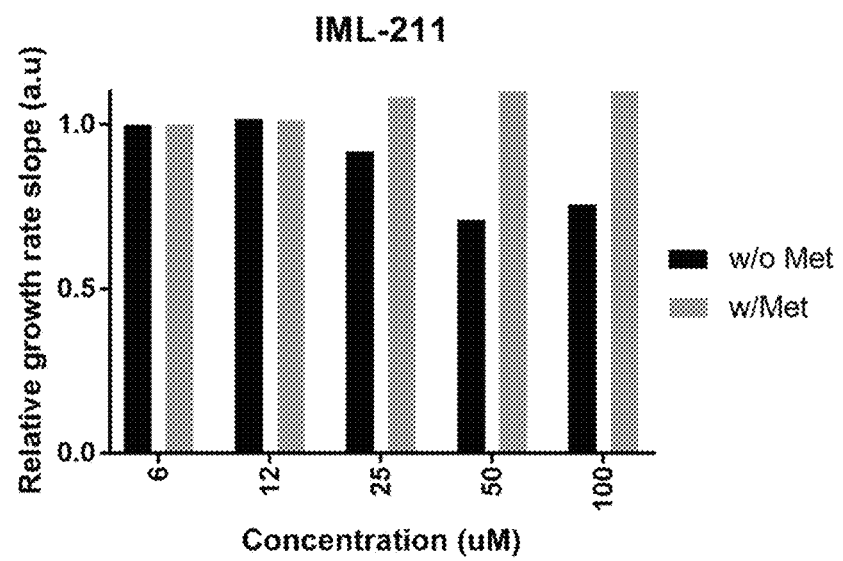
Figure 4M:
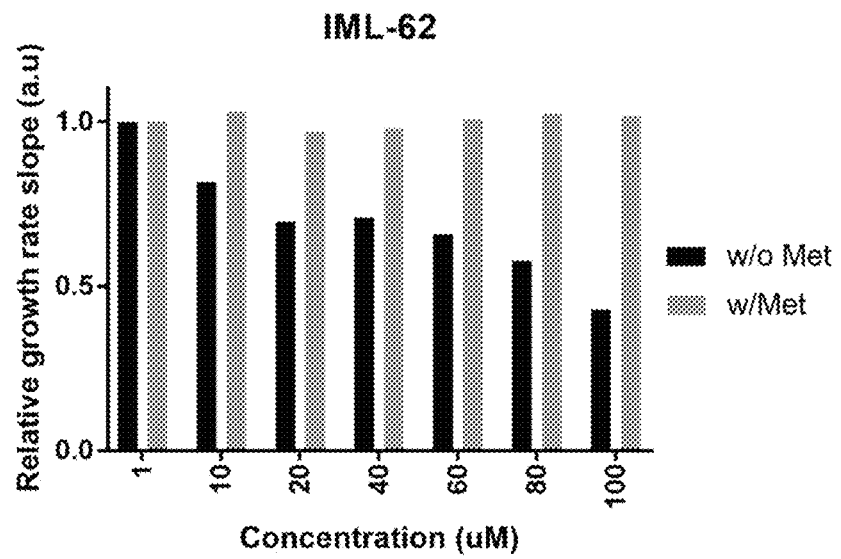
Figure 4N:
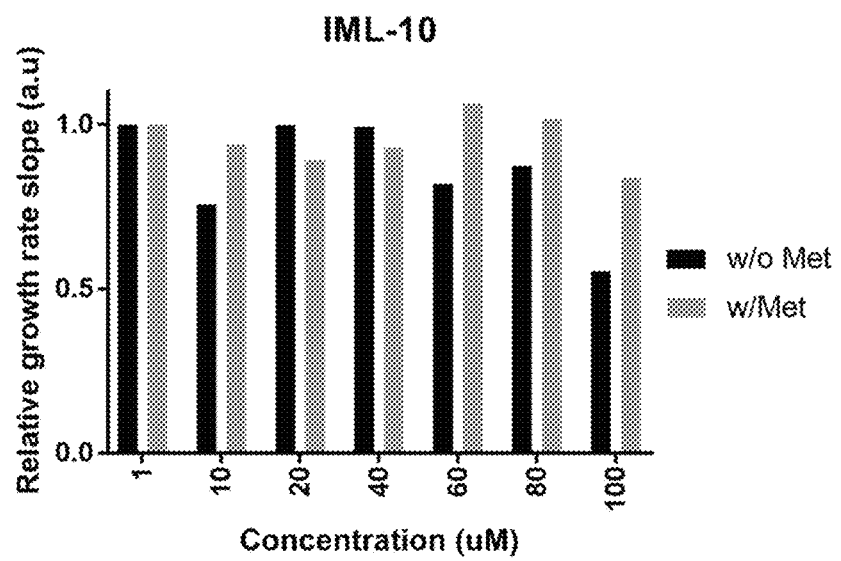
Figure 4O:
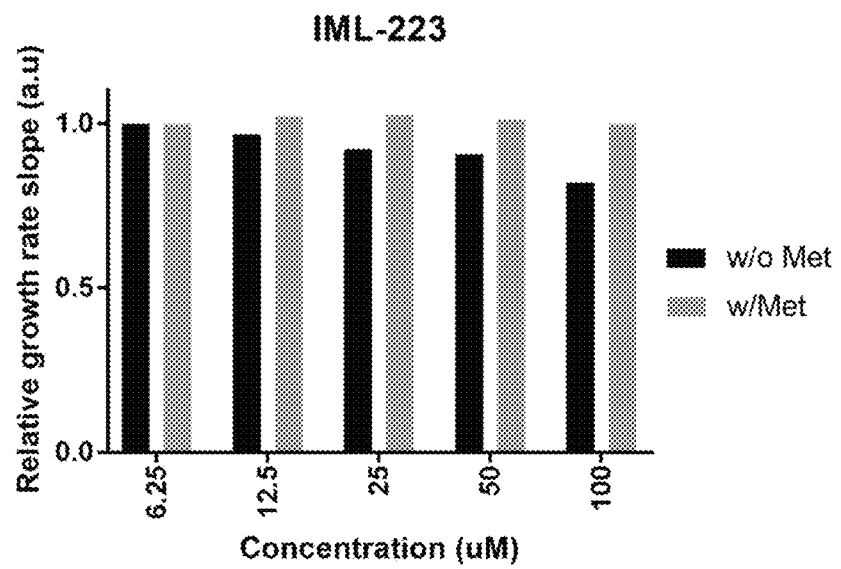
Figure 4P:
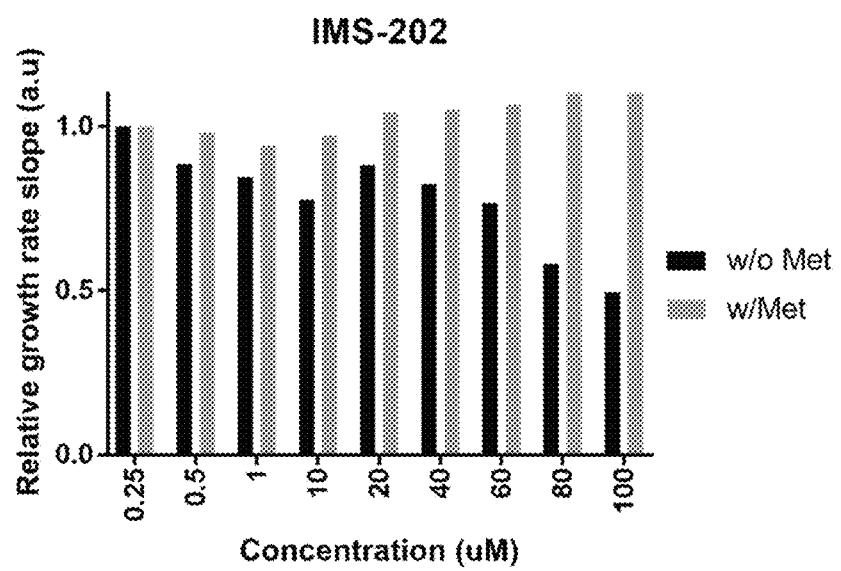
Figure 4Q:
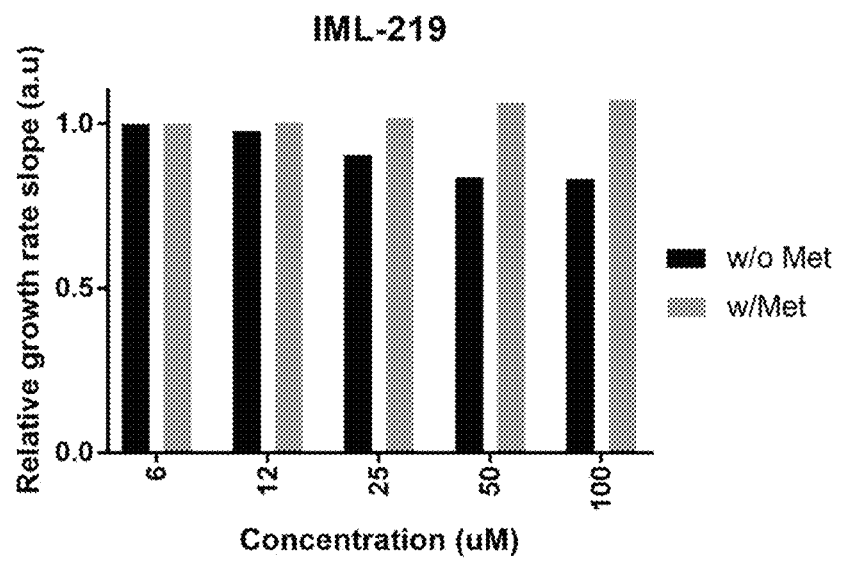
Figure 4R:
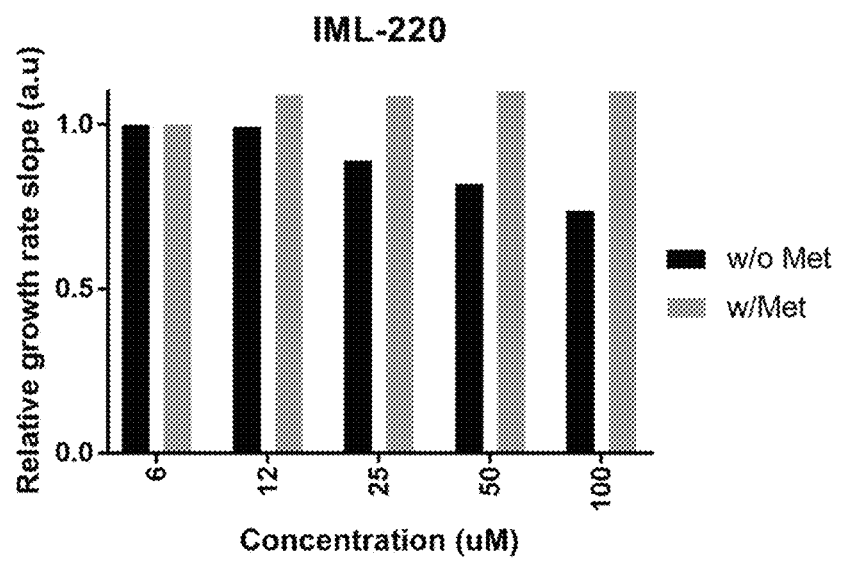
Figure 4S:
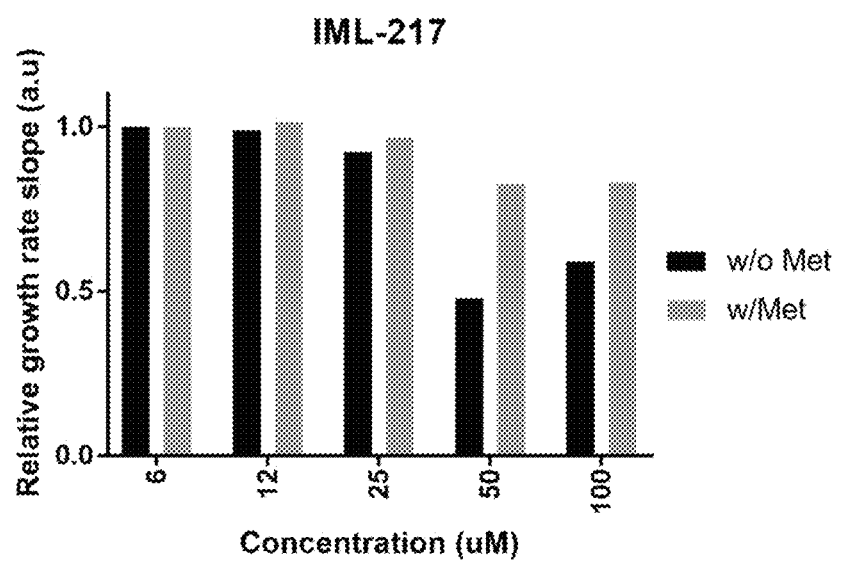

FIGS. 4a-4s demonstrate the growth rate of the engineered *E. coli* bacteria with the CGS gene of *Arabidopsis thaliana*. In this assay, Methionine auxotroph *E. coli* mutant was transformed with PQE-30 vector containing the *Arabidopsis* CGS gene as previously described in Yael Hacham et al., *Plant Physiol., February* 2002, 128(2): 454-462. In order to test the effect of the small molecule inhibitors on the CGS and methionine pathway, growth curves of the *E. coli* in M9 minimal media with 100 M IPTG were measured with and without the addition of external methionine (40 mg/L) in the presence of variable compound concentrations. *E. coli* growth curves were measured by following the optical density at 600 nm of bacteria in 96 well-plate placed within Tecan M200 plate reader in orbital shaking mode at 37° C. The slope of each curve was estimated using the 'linest' function in Excel. The results show the slope of each measured concentration relative to the lowest tested concentration.

Figure 5:
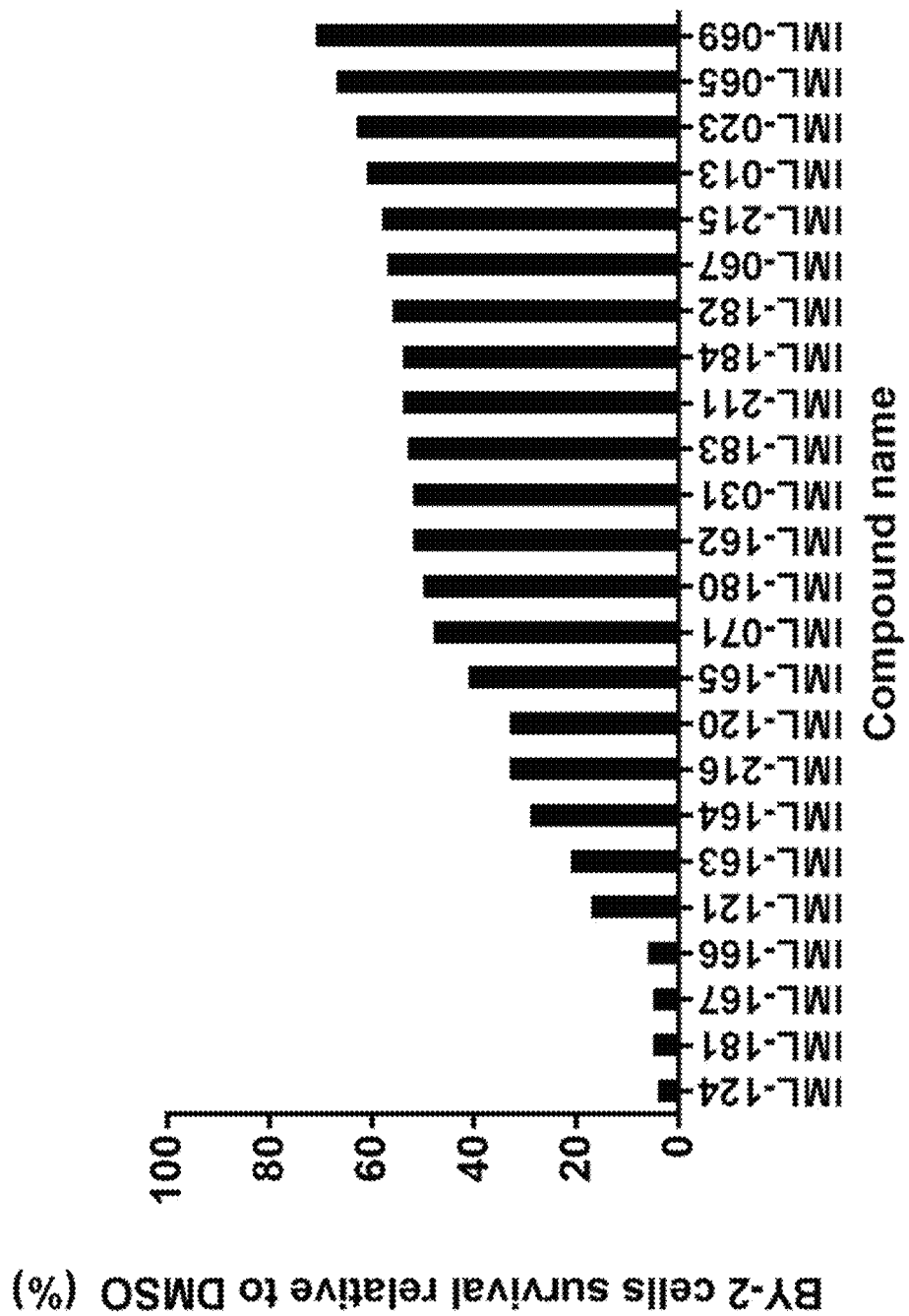
FIG. 5 shows the BY-2 cells viability assay for the compounds of the present invention.

Reference is now made to FIG. 5 showing the BY-2 viability assay. In this assay, the viability of BY2 Tobacco cells was tested following treatment with the compounds of the present invention. For this purpose, cells were cultured in Murashige and Skoog basal medium (Sigma-Aldrich, Cat # M0404), supplemented with 2,4-dichloro-phenoxyacetic acid (0.2 mg/L), and sucrose (3%), and incubated in the dark, at 25° C. and then sub-cultured at a 1:15 dilution in fresh media every 7 days.

Before treatment, the cell suspension was adjusted to OD=0.4 (at 600 nm) and seeded in 6 well plates with a volume of 3 ml per cell. The exemplified compounds were then added to the wells, at a final concentration of 25 M (0.05% DMSO), and incubated for 48 hours. Cellular viability was measured using the commercially available Presto-Blue™ assay (ThermoFisher Scientific, PrestoBlue™ Cell Viability Reagent Cat # A13261). The PrestoBlue™ reagent is a cell-permeant non-fluorescent compound, which is reduced by metabolically active cells and providing a quantitative fluorescent signal. In the assay, 10 µL of the Presto-Blue™ reagent was added to 90 µL of the treated cells and fluorescence measurements were performed done with excitation/emission wavelengths of 560/590 nm in Tecan M200 plate reader. The results show the cells viability relative to cells treated with 0.05% of DMSO only.

As discussed above, the first reaction in methionine biosynthesis in plants is catalyzed by the CGS enzyme. In this reaction, the formation of cystathionine is conducted by the γ-replacement of the phosphoryl substituent of O-phospho-homoserine by cysteine and consecutive release of an orthophosphate group. The following experiment demonstrates evaluation of the direct inhibition of a number of the compounds of the present invention on the CGS activity.

Expression of recombinant CGS was done by transforming the pET-11 vector containing the DNA sequence of Tobacco CGS with a 6xHIS tag and GB1 solubility tag followed by TEV cleavage site into BL-21 cells. These cells were cultured at 37° C. and optical density (OD)=0.8 protein at 600 nm, and the expression was induced by addition of 1 mM IPTG for 16 hours at 25° C. The protein was purified to homogeneity onto nickel column and cleaved by o/n dialysis with the TEV protease. A second nickel column was used to separate the cleaved CGS from the TEV and GB1 solubility tag.

The direct activity of CGS was tested using the Malachite Green Phosphate Assay Kit (Sigma-Aldrich, cat # MAK307-1KT). It is a highly sensitive and robust experiment used to measure the release of free orthophosphate group based on quantification of the green-coloured complex formed between Malachite Green, molybdate, and free orthophosphate. The rapid colour formation from the reaction can be conveniently measured on a spectrophotometer via the absorbance at 620 nm.

Figure 6:
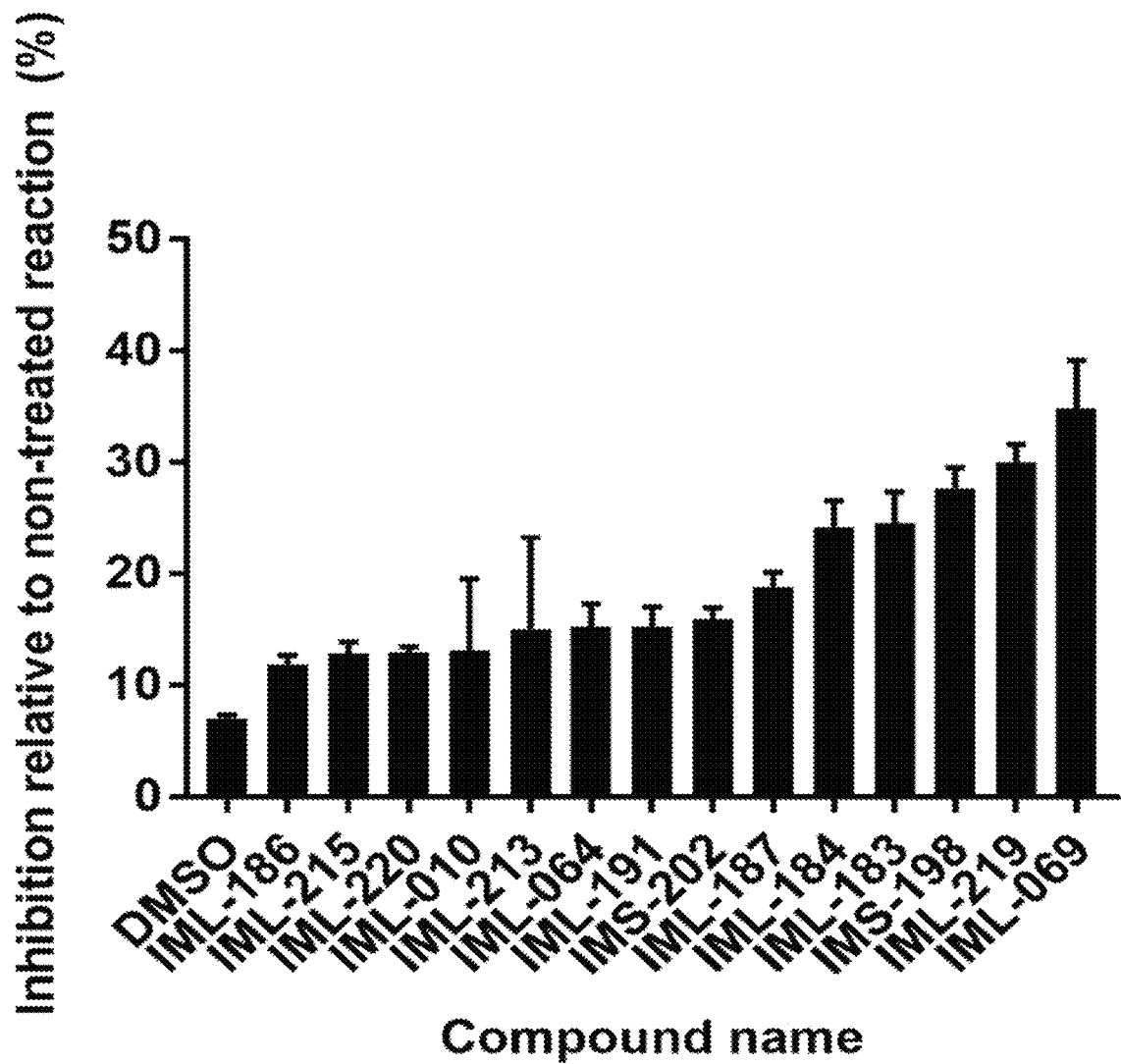
FIG. 6 shows the inhibition of the direct CGS activity relative to non-treated reaction tested using the Malachite Green Phosphate assay for the compounds of the present invention.

The assay mixture (100 µl) contained 50 mM MOPS—NaOH (pH 7.5), 150 mM NaCl, 0.1 mM PLP and 1 µM purified CGS. The compounds of the present invention were added at a final concentration of 50 µM and reactions were initiated by adding 2 mM cysteine and 3 mM O-phospho-L-homo-serine. After two-hour incubation at 25° C., 80 µL of each sample were transferred into a new 96 well-plate containing 20 µl of Malachite Green Reagent and incubated for additional 30 min at 25° C. Colour development was measured by a plate reader Tecan M200 (620 nm). FIG. 6 shows the CGS inhibition relative to non-treated reaction for a number of the compounds of the present invention.

Figure 7A:
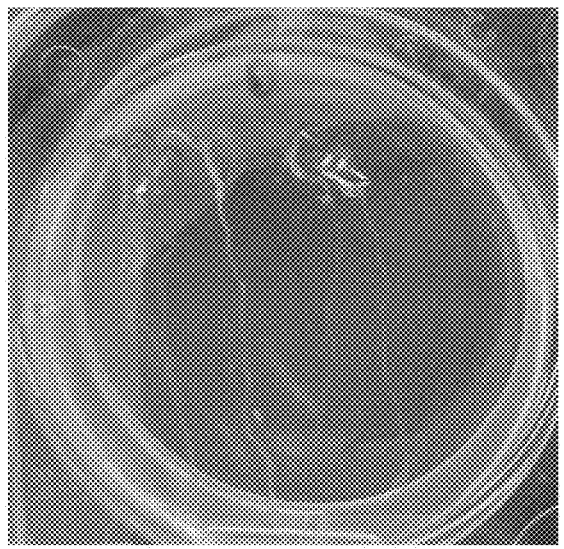
FIGS. 7a-7o show the effect of the compounds of the present invention on the inhibition of the roots growth of the Arabidopsis thaliana plants.
Figure 7A:
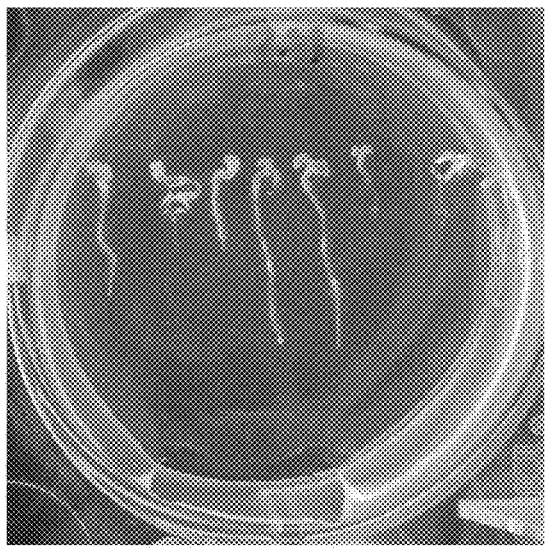
Figure 7B:
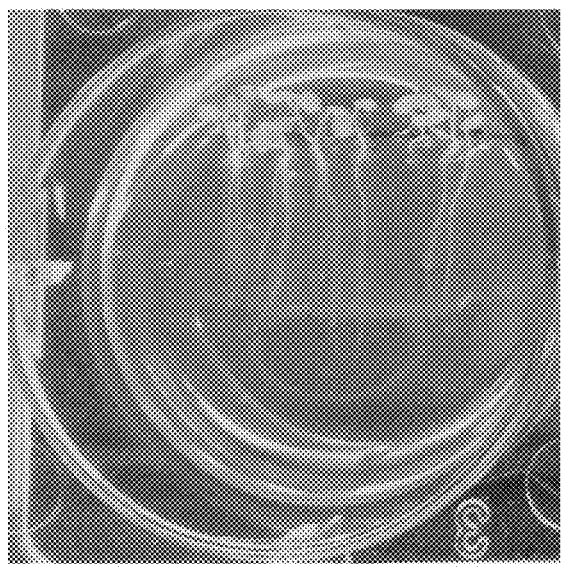
Figure 7B:
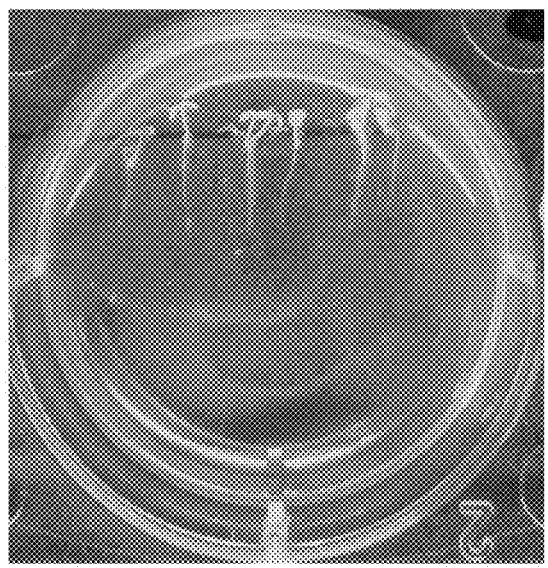
Figure 7C:
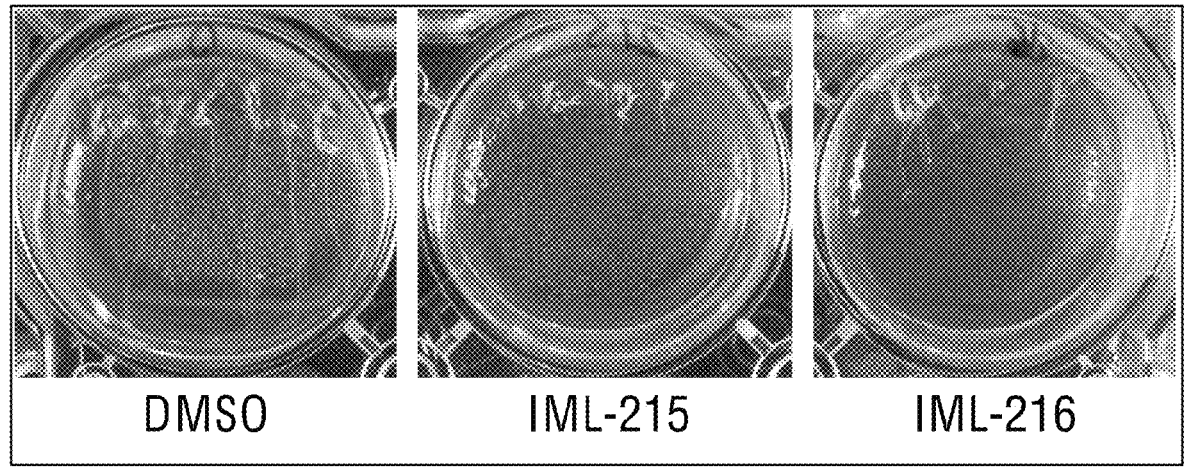
Figure 7D:
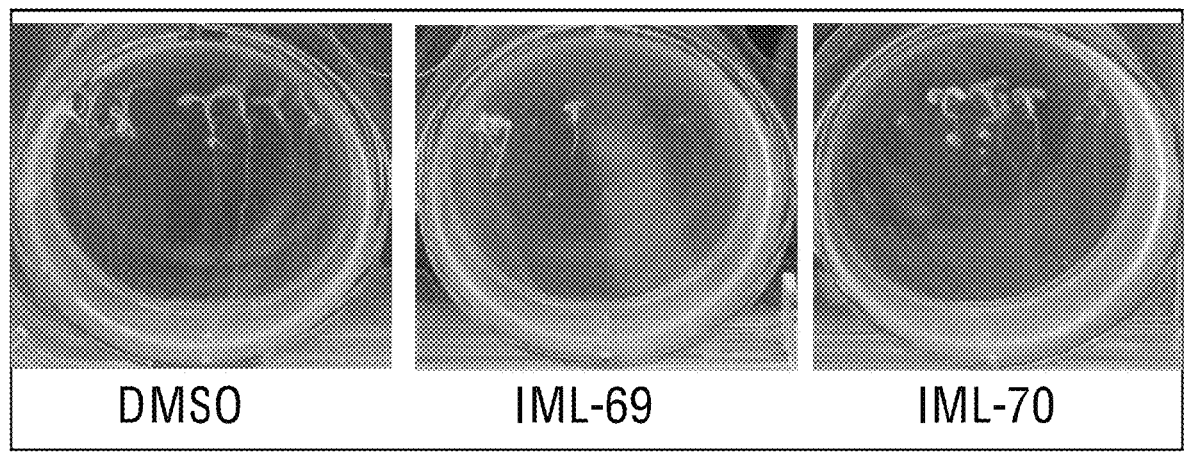
Figure 7E:
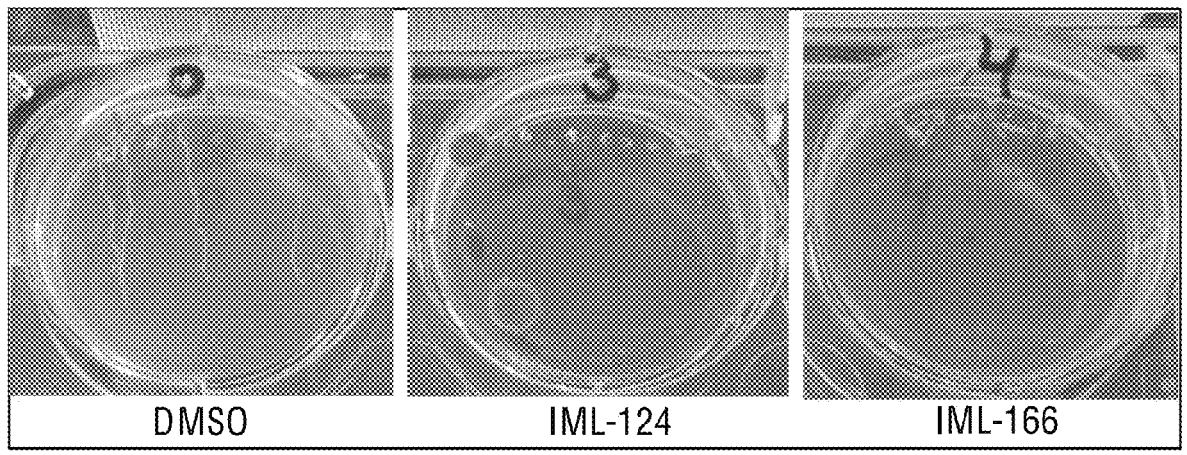
Figure 7F:
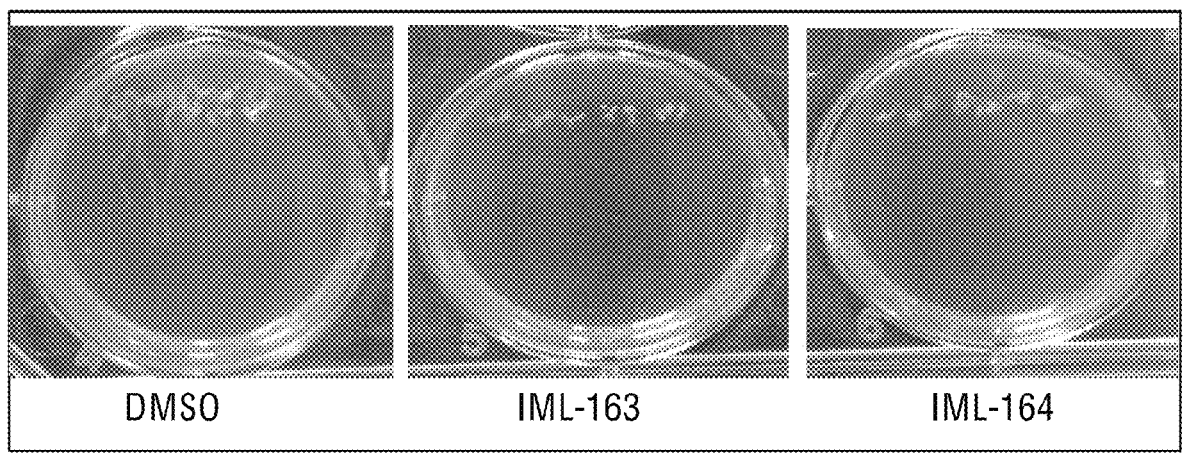
Figure 7G:
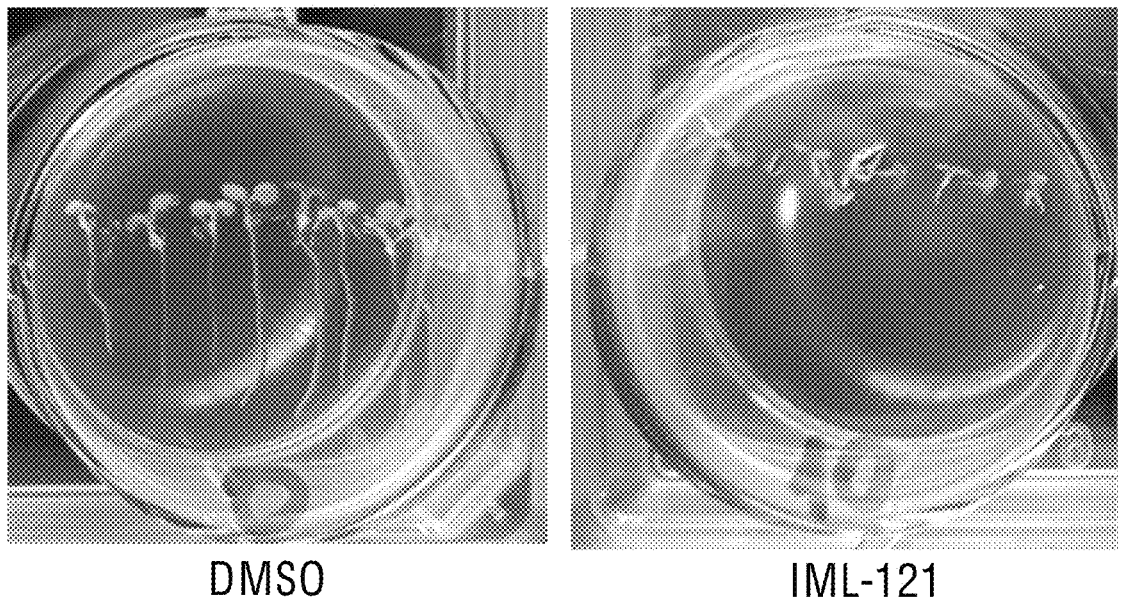
Figure 7H:
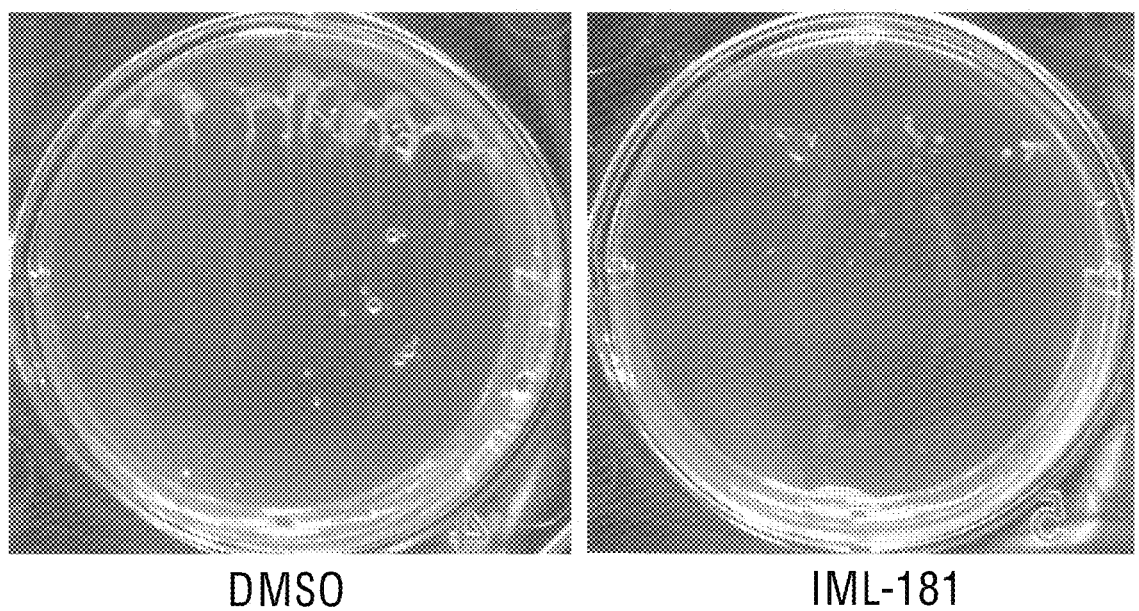
Figure 7I:
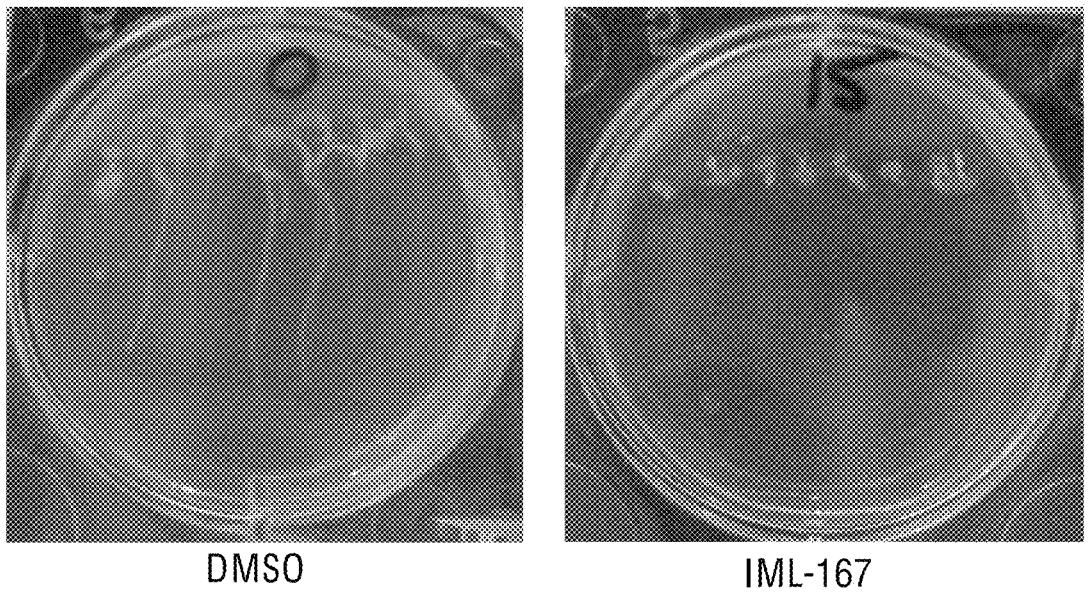
Figure 7J:
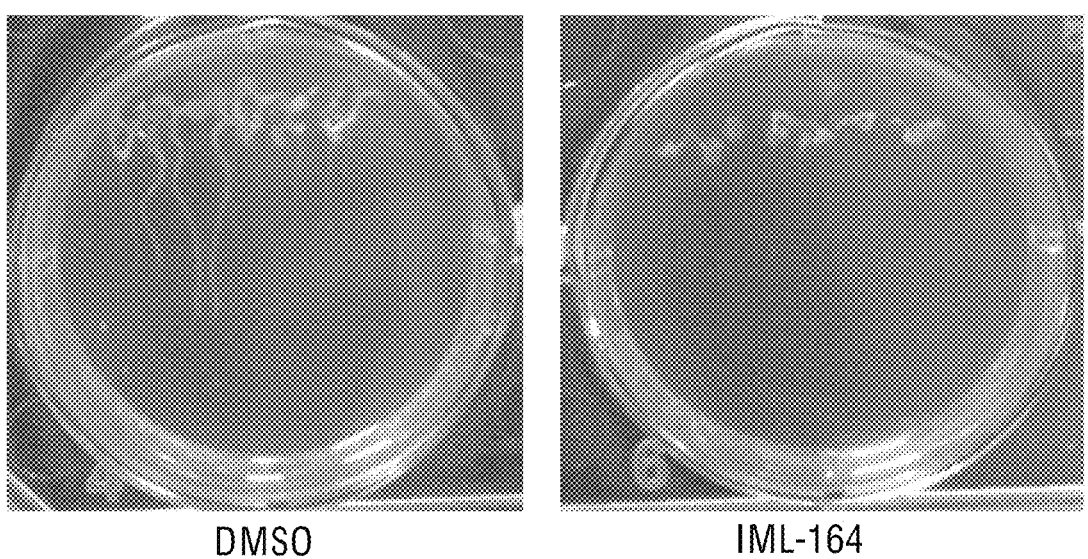
Figure 7K:
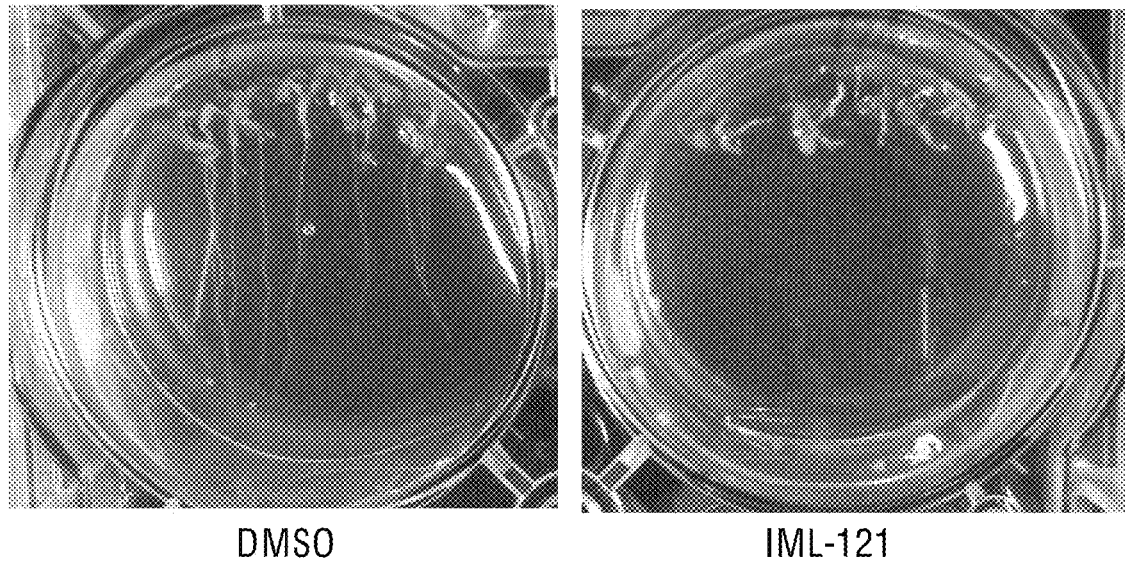
Figure 7L:
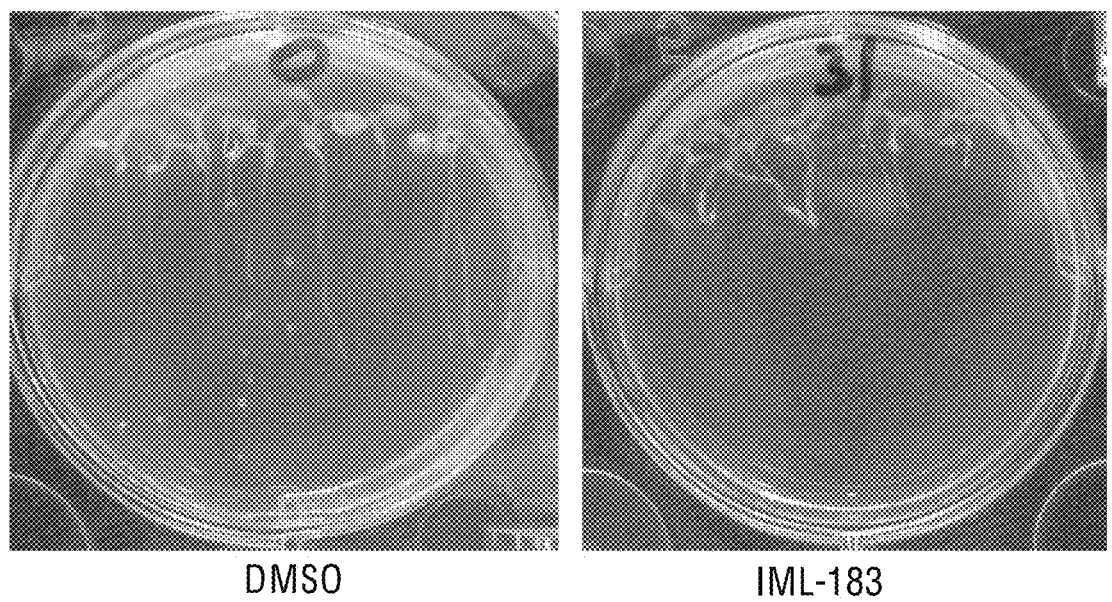
Figure 7M:
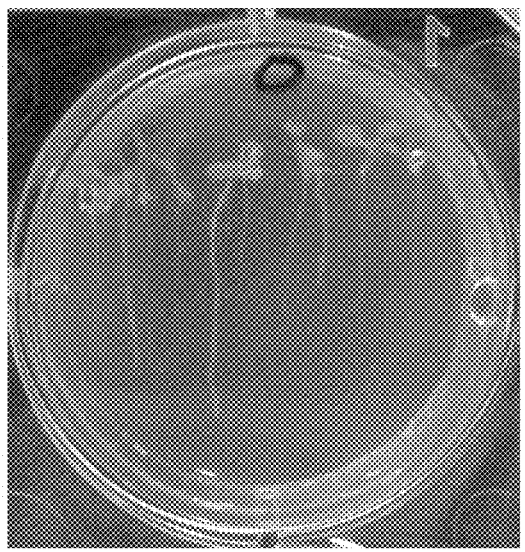
Figure 7M:
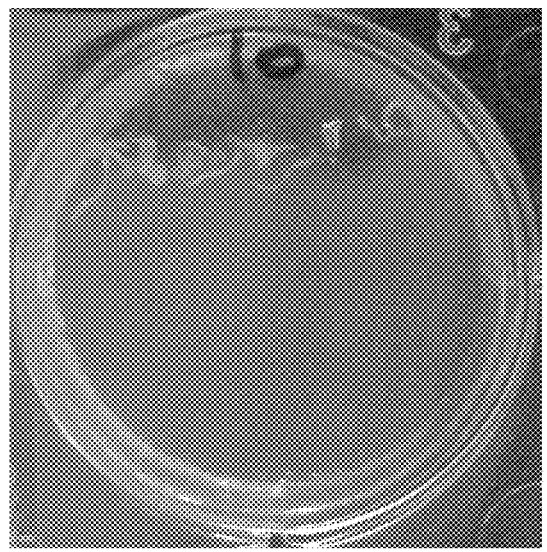
Figure 7N:
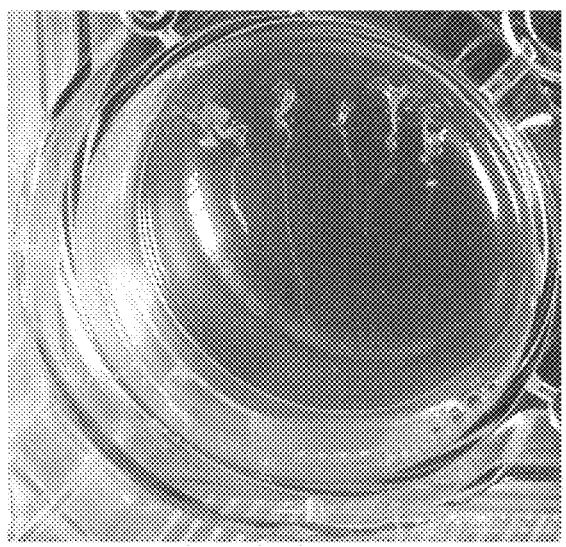
Figure 7N:
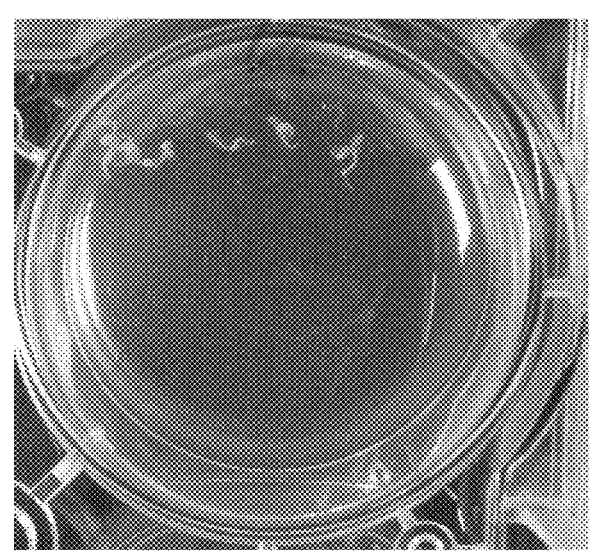
Figure 7O:
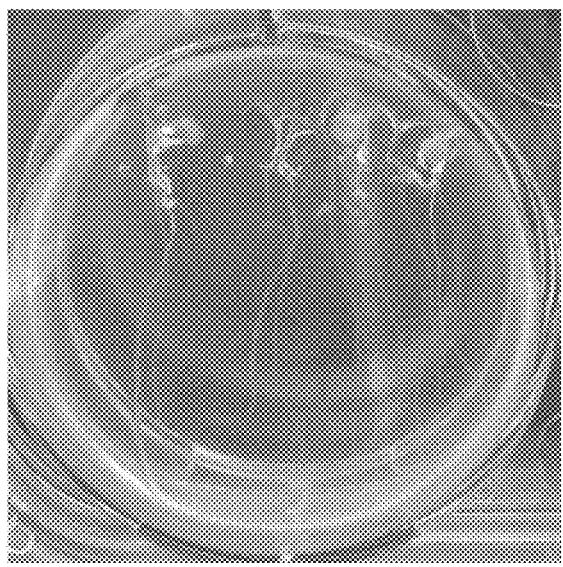
Figure 7O:
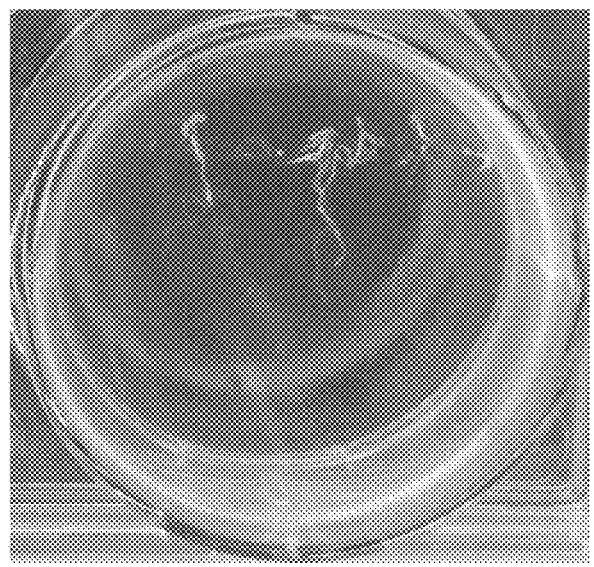

Finally, FIGS. 7a-7o are the photos of the *Arabidopsis thaliana* plants and the inhibition of their roots growth by the compounds of the present invention. These experiments were conducted as follows. Seeds were washed with 70% ethanol for one minute and then with sterile water. Sterilisation was performed with 50% bleaching solution (3%) and 0.2% Triton x-100 for ten minutes followed by a five-time wash with sterile water. The seeds were placed in six well-plates with half Murashige and Skoog medium (MS; Duchefa, Haarlem, Netherlands), containing 1% sucrose (w/v), pH 5.8. The plates with *Arabidopsis thaliana* seeds were placed at 4° C. for two days and then transferred for seven days to growth chamber (22±2° C.) at day/light cycles of 16/8 h. The plates were placed vertically. In each plate, a control including 0.1% DMSO in the medium was added. The compounds of the present invention were tested for their herbicidal efficiency by diluting 1000 times a 50 mM stock in DMSO leading to a final concentration of 50 µM with 0.1% DMSO.

Tables 1-5 below summarise the collected data on biological activity of the compounds of the present invention in the aforementioned assays.

TABLE 1
| Compound | Arabidopsis (relative to DMSO) | E. coli Assay LE395 (0-5) | E. coli specificity (MOA) | MST Tobacco (0-5) |
|---|---|---|---|---|
| 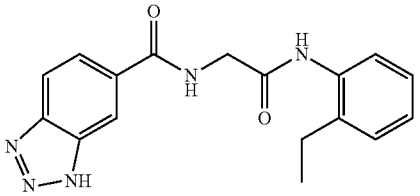 IML-102 | — | — | — | 5 |
| 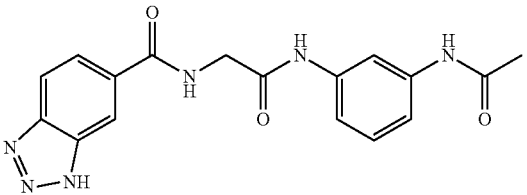 IML-110 | — | 2 | 4 | 5 |
| 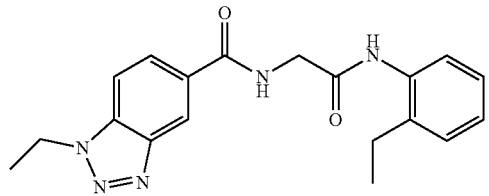 IML-112 | — | — | — | 4 |
| 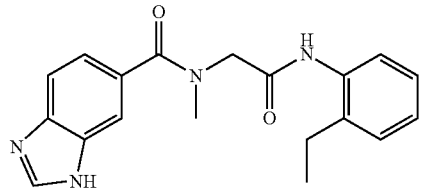 [SMILES: CCc1ccccc1NC(=O)CN(C)C(=O)c1ccc2nc[nH]c2c1] IML-113 | — | — | — | 5 |
| 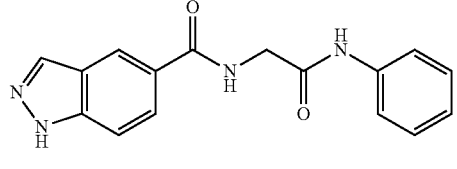 [SMILES: O=C(CNC(=O)c1ccc2[nH]ncc2c1)Nc1ccccc1] IML-134 | 0.67 | 3 | 4 | 3 |
| 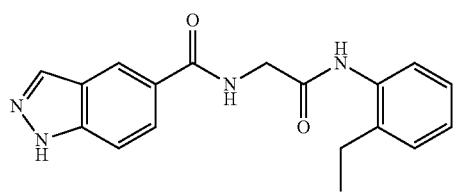 [SMILES: CCc1ccccc1NC(=O)CNC(=O)c1ccc2[nH]ncc2c1] IML-183 | — | 3 | 4 | — |
Biological activity of the compounds of Formula (IE)

TABLE 1-continued

Biological activity of the compounds of Formula (IE)

| Compound | Arabidopsis (relative to DMSO) | E. coli Assay LE395 (0-5) | E. coli specificity (MOA) | MST Tobacco (0-5) |
|---|---|---|---|---|
| 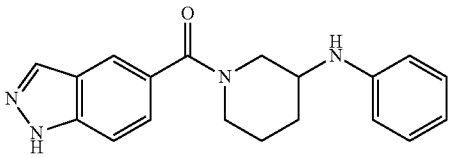 [SMILES: O=C(c1ccc2[nH]ncc2c1)N1CCCC(Nc2ccccc2)C1] IML-203 | 0.50 | — | — | — |
| 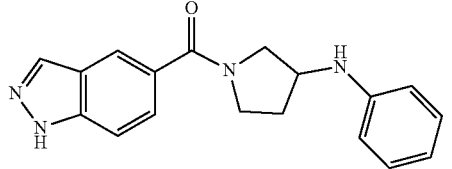 [SMILES: O=C(c1ccc2[nH]ncc2c1)N1CCC(Nc2ccccc2)C1] IML-204 | 0.35 | — | — | — |

TABLE 2

Biological activity of the compounds of Formula (ID)

| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| 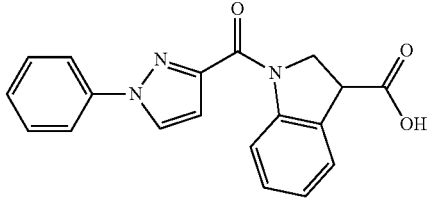 [SMILES: O=C(O)C1CN(C(=O)c2ccn(-c3ccccc3)n2)c2ccccc21] IML-121 | 0.09 | 0.28 | 4.0 | 3.0 | 30 |
| 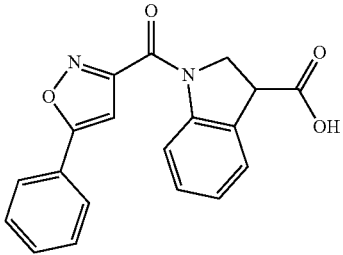 [SMILES: O=C(O)C1CN(C(=O)c2cc(-c3ccccc3)on2)c2ccccc21] IML-124 | 0.00 | 0.30 | 3.0 | — | 4 |

TABLE 2-continued
Biological activity of the compounds of Formula (ID)
| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| 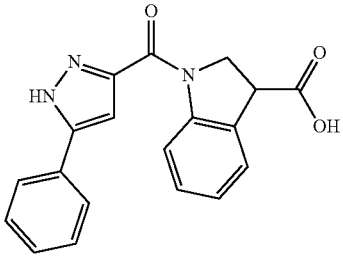 IML-125 | 0.45 | — | — | — | 58 |
| 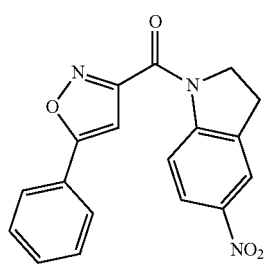 [SMILES: O=C(c1cc(-c2ccccc2)on1)N1CCc2cc([N+](=O)[O-])ccc21] IML-161 | — | 0.14 | — | — | — |
| 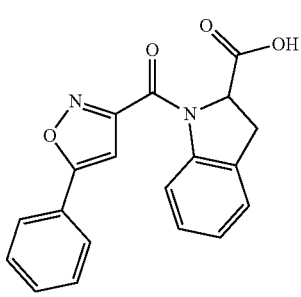 [SMILES: O=C(O)C1Cc2ccccc2N1C(=O)c1cc(-c2ccccc2)on1] IML-162 | 0.38 | 0.20 | — | 2.0 | 39 |
| 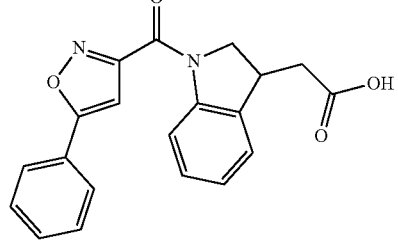 IML-163 | 0.00 | 0.31 | 4.0 | — | 21 |
| 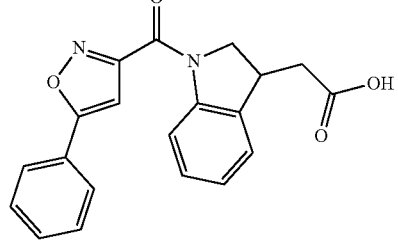 IML-164 | 0.04 | 0.11 | 3.0 | 3.0 | 21 |

TABLE 2-continued

Biological activity of the compounds of Formula (ID)

| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| IML-166 | 0.00 | 0.06 | 4.0 | 2.0 | 6 |
| IML-167 | 0.00 | 0.31 | 3.5 | 1.3 | 5 |
| IML-180 | 0.58 | 0.25 | — | — | 50 |
| IML-181 | 0.00 | 0.22 | — | 0.5 | 5 |

TABLE 2-continued

Biological activity of the compounds of Formula (ID)

| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| IML-183 | 0.23 | 0.22 | 2.0 | 3.0 | 53 |
| IML-238 | 0.03 | 0.29 | 2.0 | — | 6 |

TABLE 3

Biological activity of the compounds of Formula (ID) in *E. coli* and MST tobacco assays

| Compound | E.coli Assay LE395 (0-5) | E. coli specificity (MOA) | MST Tobacco (0-5) |
|---|---|---|---|
| IML-121 | 2 | 4 | — |
| IML-124 | 2 | 5 | — |

TABLE 3-continued

Biological activity of the compounds of Formula (ID) in *E. coli* and MST tobacco assays

| Compound | *E.coli* Assay LE395 (0-5) | *E. coli* specificity (MOA) | MST Tobacco (0-5) |
|---|---|---|---|
| IML-162 | 3 | 5 | — |
| IML-163 | 4 | 5 | — |
| IML-180 | 1 | 5 | 3 |
| IML-183 | 3 | 5 | 2 |

TABLE 4

Biological activity of the compounds of Formula (I) and Formula (IA1)

| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| IML-24 | 0.35 | — | 2.0 | — | 78 |
| IML-64 | 0.20 | 0.65 | 2.0 | 1.0 | 67 |
| IML-69 | 0.22 | 0.71 | 2.0 | 1.0 | 71 |
| IML-215 | 0.06 | 0.39 | 2.0 | 1.0 | 58 |
| IML-216 | 0.20 | 0.57 | 2.0 | 2.0 | 33 |

TABLE 4-continued

Biological activity of the compounds of Formula (I) and Formula (IA1)

| Compound | Arabidopsis (relative to DMSO) | TEV (relative to DMSO) | Roquette assay spray (twice average) | Roquette assay spray (single average) | Tobacco cells BY-2 (relative to DMSO) |
|---|---|---|---|---|---|
| IML-229 | 0.10 | 0.44 | — | — | 58 |
| IML-230 | 0.29 | — | 1.0 | — | 48 |
| IML-232 | 0.68 | — | 4.0 | 1.0 | 78 |
| IML-234 | — | 0.75 | 3.0 | 1.5 | 21 |

TABLE 5
Compounds of Formula (I) and Formula (IA1) in *E. coli*, MST tobacco and MGP assays
| Compound | *E.coli* Assay LE395 (0-5) | *E. coli* specificity (MOA) | MST Tobacco (0-5) | Malachite Green Phosphate Assay (% to DMSO, 50 μM) |
|---|---|---|---|---|
| 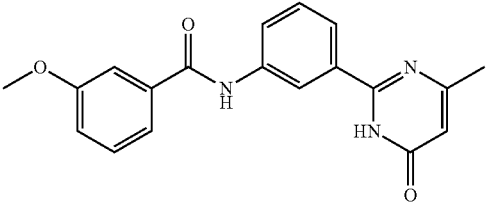 IML-11 | 3 | 4 | 3 | — |
| 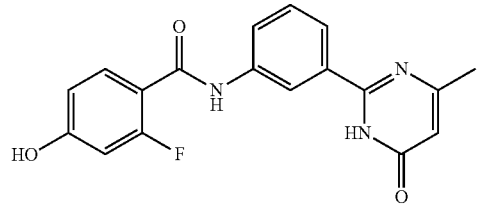 [SMILES: Cc1cc(=O)[nH]c(-c2cccc(NC(=O)c3ccc(O)cc3F)c2)n1] IML-14 | 3 | 4 | 3 | — |
| 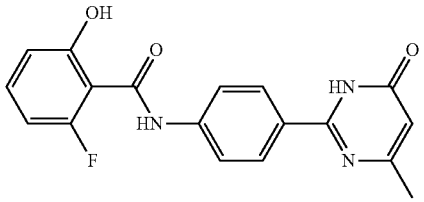 [SMILES: Cc1cc(=O)[nH]c(-c2ccc(NC(=O)c3c(O)cccc3F)cc2)n1] IML-15 | 3 | 4 | 1 | — |
| 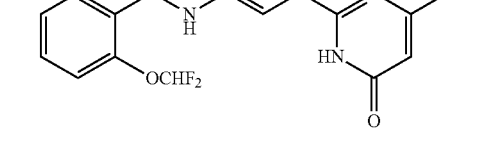 IML-22 | 2 | 4 | 3 | — |
| 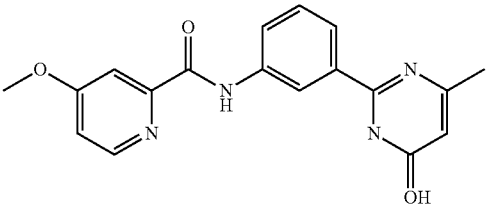 IML-62 | 3 | 5 | 4 | — |

TABLE 5-continued

Compounds of Formula (I) and Formula (IA1) in *E. coli*, MST tobacco and MGP assays

| Compound | E.coli Assay LE395 (0-5) | E. coli specificity (MOA) | MST Tobacco (0-5) | Malachite Green Phosphate Assay (% to DMSO, 50 μM) |
|---|---|---|---|---|
| IML-64 | 2 | 4 | 4 | 15.22 |
| IML-66 | 3 | 4 | 3 | — |
| IML-67 | 3 | 4 | — | — |
| IML-69 | — | — | 5 | 30 |
| IML-70 | 3 | 5 | — | — |

TABLE 5-continued
Compounds of Formula (I) and Formula (IA1) in *E. coli*, MST tobacco and MGP assays
| Compound | *E.coli* Assay LE395 (0-5) | *E. coli* specificity (MOA) | MST Tobacco (0-5) | Malachite Green Phosphate Assay (% to DMSO, 50 μM) |
|---|---|---|---|---|
| 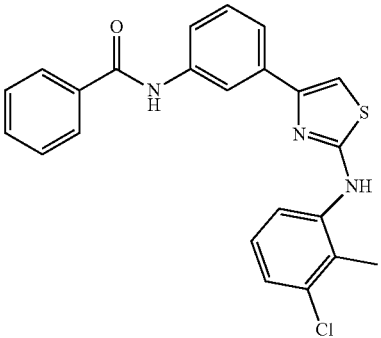 [SMILES: Cc1c(Cl)cccc1Nc1nc(-c2cccc(NC(=O)c3ccccc3)c2)cs1] IML-211 | 4 | — | — | — |
| 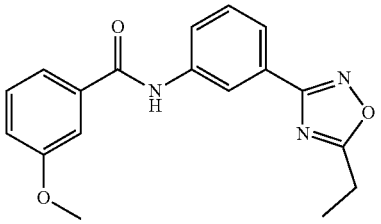 [SMILES: CCc1nc(-c2cccc(NC(=O)c3cccc(OC)c3)c2)no1] IML-215 | 3 | 3 | 2 | 12.82 |
| 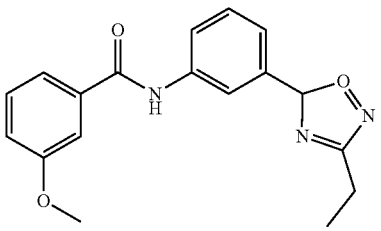 IML-216 | 3 | 5 | 2 | — |
| 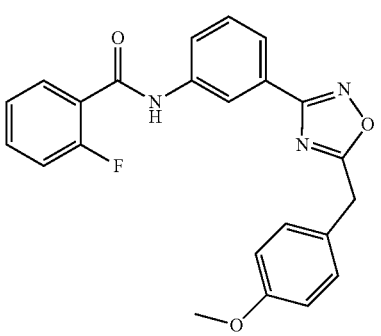 [SMILES: COc1ccc(Cc2nc(-c3cccc(NC(=O)c4ccccc4F)c3)no2)cc1] IML-217 | 3 | 5 | 2 | — |

TABLE 5-continued
Compounds of Formula (I) and Formula (IA1) in *E. coli*, MST tobacco and MGP assays
| Compound | *E.coli* Assay LE395 (0-5) | *E. coli* specificity (MOA) | MST Tobacco (0-5) | Malachite Green Phosphate Assay (% to DMSO, 50 μM) |
|---|---|---|---|---|
| 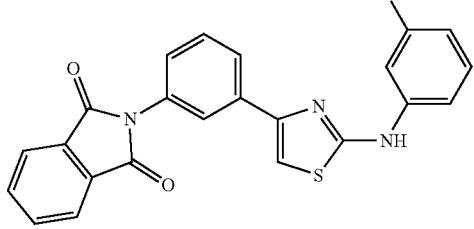 IML-218 | 3 | 5 | — | — |
| 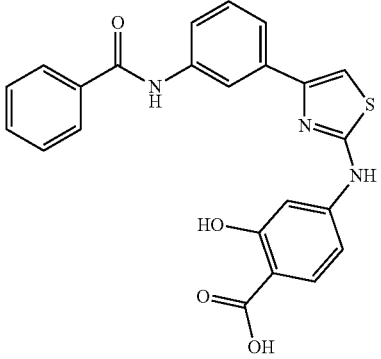 [SMILES: O=C(Nc1cccc(-c2csc(Nc3ccc(C(=O)O)c(O)c3)n2)c1)c1ccccc1] IML-219 | 1 | 5 | 4 | 28.34 |
| 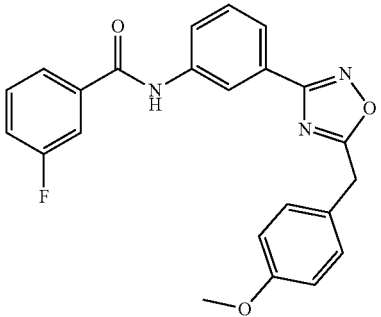 [SMILES: COc1ccc(Cc2nc(-c3cccc(NC(=O)c4cccc(F)c4)c3)no2)cc1] IML-220 | 3 | 5 | — | 10.81 |
| 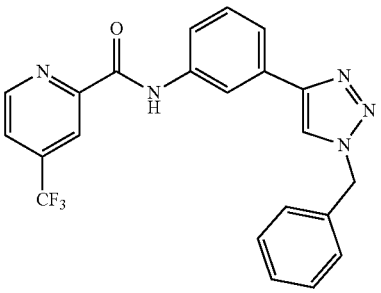 [SMILES: O=C(Nc1cccc(-c2cn(Cc3ccccc3)nn2)c1)c1cc(C(F)(F)F)ccn1] IML-223 | 5 | 5 | — | — |

TABLE 5-continued

Compounds of Formula (I) and Formula (IA1) in E. coli, MST tobacco and MGP assays

| Compound | E.coli Assay LE395 (0-5) | E. coli specificity (MOA) | MST Tobacco (0-5) | Malachite Green Phosphate Assay (% to DMSO, 50 μM) |
|---|---|---|---|---|
| IML-228 | — | — | — | 27.36 |
| IML-229 | — | — | — | 19.65 |
| IML-230 | — | — | — | 21.70 |
| IMS-220 | 4 | 5 | 3 | 15.89 |

In Tables 1, 2 and 4 above, *Arabidopsis* root length was measured after addition of 50-μM compound compared with the negative control (DMSO) treatment. Length values indicate the ratio between non-treated plates (5% DMSO only) and the length after the addition of 50 uM of each compound. Lower values indicate shorter root length, and consequently, larger effect.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A compound of Formula (ID), wherein

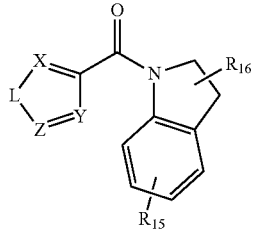

X and Y are independently CH or N;
Z is C—R$_8$ or N;
R$_8$ is hydrogen;
L is N—R$_9$;
R$_9$ is phenyl or pyridinyl optionally substituted with one to three halogen atoms;
R$_{15}$ is selected from hydrogen, halogen, nitro and carboxylic acid group; and
R$_{16}$ is hydrogen atom or carboxylic acid group.

2. The compound of claim 1 selected from:

IML-30

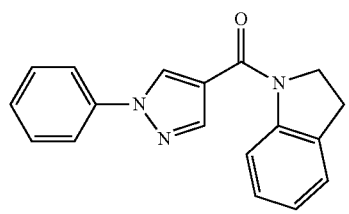

IML-33

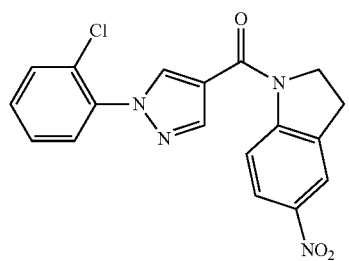

IML-31

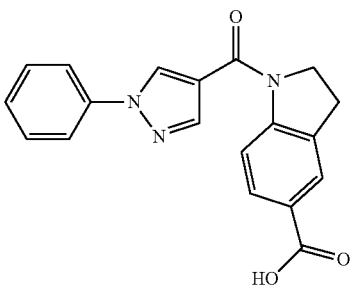

IMS-198 (7)

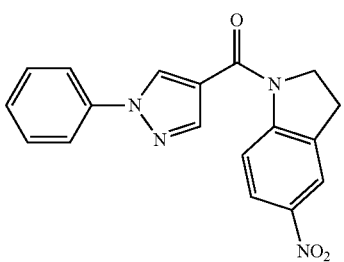

IML-32

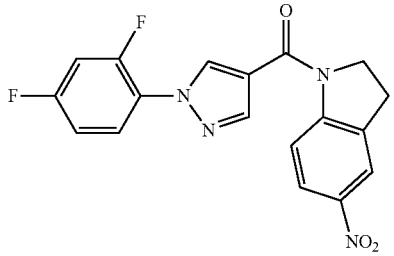

IML-162

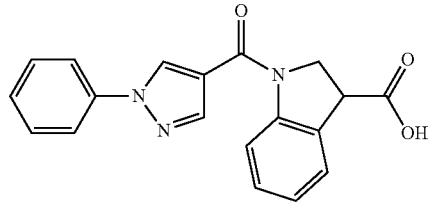

IML-120

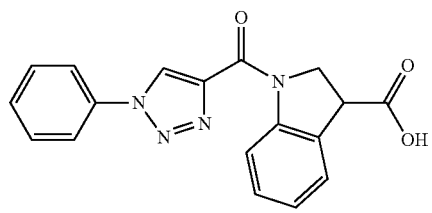

IML-121

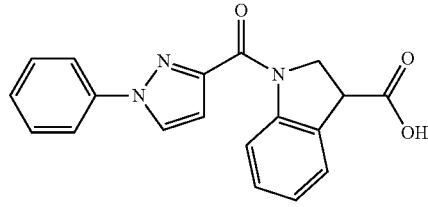

IML253

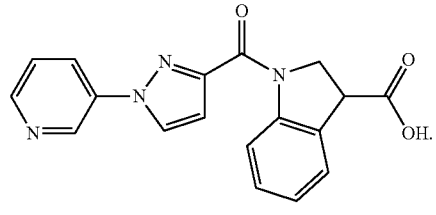

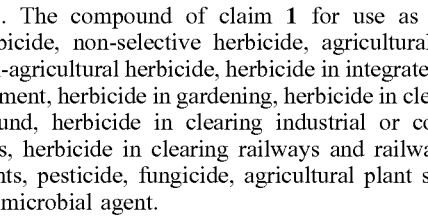

3. The compound of claim 1 for use as a selective herbicide, non-selective herbicide, agricultural herbicide, non-agricultural herbicide, herbicide in integrated pest management, herbicide in gardening, herbicide in clearing waste ground, herbicide in clearing industrial or constructions sites, herbicide in clearing railways and railway embankments, pesticide, fungicide, agricultural plant stimulant or antimicrobial agent.

4. A method for the control of undesired vegetation or clearing areas from the undesired vegetation comprising applying to the locus of said undesired vegetation, to the undesired plants or to a habitat thereof, a herbicidally effective amount of the compound of claim 1.

5. The method of claim 4, wherein said locus is agricultural areas, crop fields, gardens, waste grounds, industrial or constructions sites, railways or railway embankments.

6. The compound of claim 2 for use as a selective herbicide, non-selective herbicide, agricultural herbicide, non-agricultural herbicide, herbicide in integrated pest management, herbicide in gardening, herbicide in clearing waste ground, herbicide in clearing industrial or constructions sites, herbicide in clearing railways and railway embankments, pesticide, fungicide, agricultural plant stimulant or antimicrobial agent.

7. A method for the control of undesired vegetation or clearing areas from the undesired vegetation comprising applying to the locus of said undesired vegetation, to the undesired plants or to a habitat thereof, a herbicidally effective amount of the compound of claim 2.

* * * * *